United States Patent
Lee et al.

(10) Patent No.: US 9,243,247 B2
(45) Date of Patent: Jan. 26, 2016

(54) COMPOSITION FOR PROMOTING APOPTOSIS OR INHIBITING CELL GROWTH, COMPRISING EPSTEIN-BARR VIRUS MICRORNA

(75) Inventors: Suk Kyeong Lee, Seoul (KR); Hoyun Choi, Incheon (KR)

(73) Assignee: Catholic University Industry Academic Cooperation Foundation, Seoul (KR)

( * ) Notice: Subject to any disclaimer, the term of this patent is extended or adjusted under 35 U.S.C. 154(b) by 0 days.

(21) Appl. No.: 14/122,236

(22) PCT Filed: May 24, 2012

(86) PCT No.: PCT/KR2012/004149
§ 371 (c)(1),
(2), (4) Date: Nov. 25, 2013

(87) PCT Pub. No.: WO2012/161545
PCT Pub. Date: Nov. 29, 2012

(65) Prior Publication Data
US 2014/0296319 A1    Oct. 2, 2014

(30) Foreign Application Priority Data

May 25, 2011 (KR) .......................... 10-2011-0049812

(51) Int. Cl.
*A61K 48/00* (2006.01)
*C12N 15/113* (2010.01)
*A61K 31/713* (2006.01)
*A61K 45/06* (2006.01)

(52) U.S. Cl.
CPC ............ *C12N 15/113* (2013.01); *A61K 31/713* (2013.01); *A61K 45/06* (2013.01); *C12N 2310/141* (2013.01)

(58) Field of Classification Search
None
See application file for complete search history.

(56) References Cited

U.S. PATENT DOCUMENTS

2010/0216139 A1    8/2010    Galas et al.
2011/0033841 A1    2/2011    Lo et al.

OTHER PUBLICATIONS

Choy, Elizabeth Yee-Wai et al, "An Epstein-Barr virus-encoded microRNA targets PUMA to promote host cell survival", Journal of Experimental Medicine, (2008) vol. 205(11), pp. 2551-2560.
Seto, Eri et al, "Micro RNAs of Epstein-Barr Virus Promote Cell Cycle Progression and Prevent Apoptosis of Primary Human B Cells", PLOS Pathogens, Aug. 2010, vol. 6(8), pp. e1001063(1-16).
Thompson, Craig B., "Apoptosis in the Pathogenesis and Treatment of Disease", Science, vol. 267, pp. 1456-1462, (1995).
Fadeel, Bengt et al., "Apoptosis in Human Disease: A New Skin for the Old Ceremony?", Biochemical and Biophysical Research Communications, vol. 266 (3), pp. 699-717 (1999).
Lo, Angela Kwok Fung et al, "Modulation of LMP1 protein expression by EBV-encoded microRNAs", Proceedings of the National Academy of Sciences United States of America, vol. 104(41), pp. 16164-16169 (2007).
Lung, Raymond Wai-Ming, "Modulation of LMP2A Expression by a Newly Identified Exptein-Barr Virus-Encoded MicroRNA miR-BART22", Neoplasia, vol. 11(11), pp. 1174-1184 (2009).
Barth, Stephanie et al., "Epstein-Barr virus-encoded microRNA miR-BART2 down-regulates the viral DNA polymerase BALF5", Nucleic Acids Research, vol. 36(2), pp. 666-675 (2008).
Nachmani, Daphna et al., "Diverse Herpesvirus MicroRNAs Target the Stress-Induced Immune Ligand MICB to Escape Recognition by Natural Killer Cells", Cell Host & Microbe, vol. 5(4), pp. 376-385 (2009).
Iizasa, Hisashi et al., "RNA: Editing of Epstein-Barr Virus-encoded BART6 MicroRNAs Controls Their Dicer Targeting and Consequently Affects Viral Latency", The Journal of Biological Chemistry, vol. 285(43), pp. 33358-33370 (2010).
Marquitz, Aron R., et al., The Epstein-Barr Virus BART microRNAs target the pro-apoptotic protein Bim:, Virology, vol. 412(2), pp. 392-400 (2011).
Sui, Guangchao et al., "A DNA vector-based RNAi technology to supress gene expression in mammalian cells", Proceedings of the National Academy of Science United States of America, vol. 99(8), pp. 5515-5520 (2002).
Brummelkamp, Thijn R., et al., "A System for Stable Expression of Short Interfering RNAs in Mammalian Cells", Science, Apr. 19, 2002, vol. 296, pp. 550-553.
Paul, Cynthia P., et al., "Effective expression of small interfering RNA in human cells", Nature Biotechnology, May 2002, vol. 20, pp. 505-508.
Choi, Hoyun, et al., "Epstein-Barr Virus-Encoded MicroRNA BART15-3p Promotes Cell Apoptosis Partially by Targeting BRUCE", Journal of Virology, Jul. 1, 2013, vol. 87(14) pp. 8135-8144.
International Search Report and Written Opinion in PCT/KR2012/004149 dated Dec. 20, 2012.

*Primary Examiner* — Kimberly Chong
(74) *Attorney, Agent, or Firm* — Nixon Peabody LLP; Robert E. Krebs

(57) ABSTRACT

Provided is a use of an miRNA of an Epstein-Barr virus (EBV), more specifically, EBV miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, miR-BART2-3p, and mimics thereof for promoting apoptosis or inhibiting cell growth.

3 Claims, 10 Drawing Sheets

SEQUENCE LISTING

```
<160> NUMBER OF SEQ ID NOS: 88

<210> SEQ ID NO 1
<211> LENGTH: 21
<212> TYPE: RNA
<213> ORGANISM: Artificial Sequence
<220> FEATURE:
<223> OTHER INFORMATION: ebv-miR-BART3-5p (sense)

<400> SEQUENCE: 1
accuaguguu aguguugugc u                                            21

<210> SEQ ID NO 2
<211> LENGTH: 21
<212> TYPE: RNA
<213> ORGANISM: Artificial Sequence
<220> FEATURE:
<223> OTHER INFORMATION: ebv-miR-BART3-5p (antisense)

<400> SEQUENCE: 2
agcacaacac uaacacuagg u                                            21

<210> SEQ ID NO 3
<211> LENGTH: 22
<212> TYPE: RNA
<213> ORGANISM: Artificial Sequence
<220> FEATURE:
<223> OTHER INFORMATION: ebv-miR-BART3-3p (sense)

<400> SEQUENCE: 3
cgcaccacua gucaccaggu gu                                           22

<210> SEQ ID NO 4
<211> LENGTH: 22
<212> TYPE: RNA
<213> ORGANISM: Artificial Sequence
<220> FEATURE:
<223> OTHER INFORMATION: ebv-miR-BART3-3p (antisense)

<400> SEQUENCE: 4
acaccuggug acuaguggug cg                                           22

<210> SEQ ID NO 5
<211> LENGTH: 22
<212> TYPE: RNA
<213> ORGANISM: Artificial Sequence
<220> FEATURE:
<223> OTHER INFORMATION: ebv-miR-BART4-5p (sense)

<400> SEQUENCE: 5
gaccugaugc ugcuggugug cu                                           22
```

```
<210> SEQ ID NO 6
<211> LENGTH: 22
<212> TYPE: RNA
<213> ORGANISM: Artificial Sequence
<220> FEATURE:
<223> OTHER INFORMATION: ebv-miR-BART4-5p (antisense)

<400> SEQUENCE: 6
agcacaccag cagcaucagg uc                                              22

<210> SEQ ID NO 7
<211> LENGTH: 23
<212> TYPE: RNA
<213> ORGANISM: Artificial Sequence
<220> FEATURE:
<223> OTHER INFORMATION: ebv-miR-BART4-3p (sense)

<400> SEQUENCE: 7
cacaucacgu aggcaccagg ugu                                             23

<210> SEQ ID NO 8
<211> LENGTH: 23
<212> TYPE: RNA
<213> ORGANISM: Artificial Sequence
<220> FEATURE:
<223> OTHER INFORMATION: ebv-miR-BART4-3p (antisense)

<400> SEQUENCE: 8
acaccuggug ccuacgugau gug                                             23

<210> SEQ ID NO 9
<211> LENGTH: 24
<212> TYPE: RNA
<213> ORGANISM: Artificial Sequence
<220> FEATURE:
<223> OTHER INFORMATION: ebv-miR-BART1-5p (sense)

<400> SEQUENCE: 9
ucuuagugga agugacgugc ugug                                            24

<210> SEQ ID NO 10
<211> LENGTH: 24
<212> TYPE: RNA
<213> ORGANISM: Artificial Sequence
<220> FEATURE:
<223> OTHER INFORMATION: ebv-miR-BART1-5p (antisense)

<400> SEQUENCE: 10
cacagcacgu cacuuccacu aaga                                            24

<210> SEQ ID NO 11
<211> LENGTH: 22
<212> TYPE: RNA
<213> ORGANISM: Artificial Sequence
<220> FEATURE:
<223> OTHER INFORMATION: ebv-miR-BART1-3p (sense)

<400> SEQUENCE: 11
uagcaccgcu auccacuaug uc                                              22

<210> SEQ ID NO 12
<211> LENGTH: 22
<212> TYPE: RNA
<213> ORGANISM: Artificial Sequence
<220> FEATURE:
<223> OTHER INFORMATION: ebv-miR-BART1-3p (antisense)
```

-continued

```
<400> SEQUENCE: 12
gacauagugg auagcggugc ua                                                  22

<210> SEQ ID NO 13
<211> LENGTH: 24
<212> TYPE: RNA
<213> ORGANISM: Artificial Sequence
<220> FEATURE:
<223> OTHER INFORMATION: ebv-miR-BART15-5p (sense)

<400> SEQUENCE: 13
agggaaacau gaccaccuga aguc                                                24

<210> SEQ ID NO 14
<211> LENGTH: 24
<212> TYPE: RNA
<213> ORGANISM: Artificial Sequence
<220> FEATURE:
<223> OTHER INFORMATION: ebv-miR-BART15-5p (antisense)

<400> SEQUENCE: 14
gacuucaggu ggucauguuu cccu                                                24

<210> SEQ ID NO 15
<211> LENGTH: 22
<212> TYPE: RNA
<213> ORGANISM: Artificial Sequence
<220> FEATURE:
<223> OTHER INFORMATION: ebv-miR-BART15-3p (sense)

<400> SEQUENCE: 15
gucagugguu uuguuccuu ga                                                   22

<210> SEQ ID NO 16
<211> LENGTH: 22
<212> TYPE: RNA
<213> ORGANISM: Artificial Sequence
<220> FEATURE:
<223> OTHER INFORMATION: ebv-miR-BART15-3p (antisense)

<400> SEQUENCE: 16
ucaaggaaac aaaaccacug ac                                                  22

<210> SEQ ID NO 17
<211> LENGTH: 24
<212> TYPE: RNA
<213> ORGANISM: Artificial Sequence
<220> FEATURE:
<223> OTHER INFORMATION: ebv-miR-BART5-5p (sense)

<400> SEQUENCE: 17
caaggugaau auagcugccc aucg                                                24

<210> SEQ ID NO 18
<211> LENGTH: 24
<212> TYPE: RNA
<213> ORGANISM: Artificial Sequence
<220> FEATURE:
<223> OTHER INFORMATION: ebv-miR-BART5-5p (antisense)

<400> SEQUENCE: 18
cgaugggcag cuauauucac cuug                                                24

<210> SEQ ID NO 19
<211> LENGTH: 18
```

```
<212> TYPE: RNA
<213> ORGANISM: Artificial Sequence
<220> FEATURE:
<223> OTHER INFORMATION: ebv-miR-BART5-3p (sense)

<400> SEQUENCE: 19
gugggccgcu guucaccu                                            18

<210> SEQ ID NO 20
<211> LENGTH: 18
<212> TYPE: RNA
<213> ORGANISM: Artificial Sequence
<220> FEATURE:
<223> OTHER INFORMATION: ebv-miR-BART5-3p (antisense)

<400> SEQUENCE: 20
aggugaacag cggcccac                                            18

<210> SEQ ID NO 21
<211> LENGTH: 24
<212> TYPE: RNA
<213> ORGANISM: Artificial Sequence
<220> FEATURE:
<223> OTHER INFORMATION: ebv-miR-BART16-5p (sense)

<400> SEQUENCE: 21
uuagauagag ugggugugug cucu                                     24

<210> SEQ ID NO 22
<211> LENGTH: 24
<212> TYPE: RNA
<213> ORGANISM: Artificial Sequence
<220> FEATURE:
<223> OTHER INFORMATION: ebv-miR-BART16-5p (antisense)

<400> SEQUENCE: 22
agagcacaca cccacucuau cuaa                                     24

<210> SEQ ID NO 23
<211> LENGTH: 21
<212> TYPE: RNA
<213> ORGANISM: Artificial Sequence
<220> FEATURE:
<223> OTHER INFORMATION: ebv-miR-BART16-3p (sense)

<400> SEQUENCE: 23
aucaccaccc ucuauccaua u                                        21

<210> SEQ ID NO 24
<211> LENGTH: 21
<212> TYPE: RNA
<213> ORGANISM: Artificial Sequence
<220> FEATURE:
<223> OTHER INFORMATION: ebv-miR-BART16-3p (antisense)

<400> SEQUENCE: 24
auauggauag agggugguga u                                        21

<210> SEQ ID NO 25
<211> LENGTH: 22
<212> TYPE: RNA
<213> ORGANISM: Artificial Sequence
<220> FEATURE:
<223> OTHER INFORMATION: ebv-miR-BART17-5p (sense)

<400> SEQUENCE: 25
```
uaagaggacg caggcauaca ag                                                22

<210> SEQ ID NO 26
<211> LENGTH: 22
<212> TYPE: RNA
<213> ORGANISM: Artificial Sequence
<220> FEATURE:
<223> OTHER INFORMATION: ebv-miR-BART17-5p (antisense)

<400> SEQUENCE: 26
cuuguaugcc ugcguccucu ua                                                22

<210> SEQ ID NO 27
<211> LENGTH: 23
<212> TYPE: RNA
<213> ORGANISM: Artificial Sequence
<220> FEATURE:
<223> OTHER INFORMATION: ebv-miR-BART17-3p (sense)

<400> SEQUENCE: 27
uguaugccug gugucccuu agu                                                23

<210> SEQ ID NO 28
<211> LENGTH: 23
<212> TYPE: RNA
<213> ORGANISM: Artificial Sequence
<220> FEATURE:
<223> OTHER INFORMATION: ebv-miR-BART17-3p (antisense)

<400> SEQUENCE: 28
acuaagggga caccaggcau aca                                               23

<210> SEQ ID NO 29
<211> LENGTH: 22
<212> TYPE: RNA
<213> ORGANISM: Artificial Sequence
<220> FEATURE:
<223> OTHER INFORMATION: ebv-miR-BART6-5p (sense)

<400> SEQUENCE: 29
uaagguuggu ccaauccaua gg                                                22

<210> SEQ ID NO 30
<211> LENGTH: 22
<212> TYPE: RNA
<213> ORGANISM: Artificial Sequence
<220> FEATURE:
<223> OTHER INFORMATION: ebv-miR-BART6-5p (antisense)

<400> SEQUENCE: 30
ccuauggauu ggaccaaccu ua                                                22

<210> SEQ ID NO 31
<211> LENGTH: 22
<212> TYPE: RNA
<213> ORGANISM: Artificial Sequence
<220> FEATURE:
<223> OTHER INFORMATION: ebv-miR-BART6-3p (sense)

<400> SEQUENCE: 31
cggggaucgg acuagccuua ga                                                22

<210> SEQ ID NO 32
<211> LENGTH: 22
<212> TYPE: RNA
<213> ORGANISM: Artificial Sequence

```
<220> FEATURE:
<223> OTHER INFORMATION: ebv-miR-BART6-3p (antisense)

<400> SEQUENCE: 32
ucuaaggcua guccgauccc cg                                              22

<210> SEQ ID NO 33
<211> LENGTH: 21
<212> TYPE: RNA
<213> ORGANISM: Artificial Sequence
<220> FEATURE:
<223> OTHER INFORMATION: ebv-miR-BART21-5p (sense)

<400> SEQUENCE: 33
ucacuaguga aggcaacuaa c                                               21

<210> SEQ ID NO 34
<211> LENGTH: 21
<212> TYPE: RNA
<213> ORGANISM: Artificial Sequence
<220> FEATURE:
<223> OTHER INFORMATION: ebv-miR-BART21-5p (antisense)

<400> SEQUENCE: 34
guuaguugcc uucacuagug a                                               21

<210> SEQ ID NO 35
<211> LENGTH: 22
<212> TYPE: RNA
<213> ORGANISM: Artificial Sequence
<220> FEATURE:
<223> OTHER INFORMATION: ebv-miR-BART21-3p (sense)

<400> SEQUENCE: 35
cuaguugugc ccacuggugu uu                                              22

<210> SEQ ID NO 36
<211> LENGTH: 22
<212> TYPE: RNA
<213> ORGANISM: Artificial Sequence
<220> FEATURE:
<223> OTHER INFORMATION: ebv-miR-BART21-3p (antisense)

<400> SEQUENCE: 36
aaacaccagu gggcacaacu ag                                              22

<210> SEQ ID NO 37
<211> LENGTH: 22
<212> TYPE: RNA
<213> ORGANISM: Artificial Sequence
<220> FEATURE:
<223> OTHER INFORMATION: ebv-miR-BART18-5p (sense)

<400> SEQUENCE: 37
ucaaguucgc acuuccuaua ca                                              22

<210> SEQ ID NO 38
<211> LENGTH: 22
<212> TYPE: RNA
<213> ORGANISM: Artificial Sequence
<220> FEATURE:
<223> OTHER INFORMATION: ebv-miR-BART18-5p (antisene)

<400> SEQUENCE: 38
uguauaggaa gugcgaacuu ga                                              22
```

<210> SEQ ID NO 39
<211> LENGTH: 22
<212> TYPE: RNA
<213> ORGANISM: Artificial Sequence
<220> FEATURE:
<223> OTHER INFORMATION: ebv-miR-BART18-3p (sense)

<400> SEQUENCE: 39
uaucggaagu uugggcuucg uc                                              22

<210> SEQ ID NO 40
<211> LENGTH: 22
<212> TYPE: RNA
<213> ORGANISM: Artificial Sequence
<220> FEATURE:
<223> OTHER INFORMATION: ebv-miR-BART18-3p (antisense)

<400> SEQUENCE: 40
gacgaagccc aaacuuccga ua                                              22

<210> SEQ ID NO 41
<211> LENGTH: 22
<212> TYPE: RNA
<213> ORGANISM: Artificial Sequence
<220> FEATURE:
<223> OTHER INFORMATION: ebv-miR-BART7-5p (sense)

<400> SEQUENCE: 41
ccuggaccuu gacuaugaaa ca                                              22

<210> SEQ ID NO 42
<211> LENGTH: 22
<212> TYPE: RNA
<213> ORGANISM: Artificial Sequence
<220> FEATURE:
<223> OTHER INFORMATION: ebv-miR-BART7-5p (antisene)

<400> SEQUENCE: 42
uguuucauag ucaaggucca gg                                              22

<210> SEQ ID NO 43
<211> LENGTH: 22
<212> TYPE: RNA
<213> ORGANISM: Artificial Sequence
<220> FEATURE:
<223> OTHER INFORMATION: ebv-miR-BART7-3p (sense)

<400> SEQUENCE: 43
caucauaguc caguguccag gg                                              22

<210> SEQ ID NO 44
<211> LENGTH: 22
<212> TYPE: RNA
<213> ORGANISM: Artificial Sequence
<220> FEATURE:
<223> OTHER INFORMATION: ebv-miR-BART7-3p (antisense)

<400> SEQUENCE: 44
cccuggacac uggacuauga ug                                              22

<210> SEQ ID NO 45
<211> LENGTH: 22
<212> TYPE: RNA
<213> ORGANISM: Artificial Sequence
<220> FEATURE:
<223> OTHER INFORMATION: ebv-miR-BART8-5p (sense)

-continued

```
<400> SEQUENCE: 45
uacgguuucc uagauuguac ag                                          22

<210> SEQ ID NO 46
<211> LENGTH: 22
<212> TYPE: RNA
<213> ORGANISM: Artificial Sequence
<220> FEATURE:
<223> OTHER INFORMATION: ebv-miR-BART8-5p (antisense)

<400> SEQUENCE: 46
cuguacaauc uaggaaaccg ua                                          22

<210> SEQ ID NO 47
<211> LENGTH: 23
<212> TYPE: RNA
<213> ORGANISM: Artificial Sequence
<220> FEATURE:
<223> OTHER INFORMATION: ebv-miR-BART8-3p (sense)

<400> SEQUENCE: 47
gucacaaucu augggucgu aga                                          23

<210> SEQ ID NO 48
<211> LENGTH: 23
<212> TYPE: RNA
<213> ORGANISM: Artificial Sequence
<220> FEATURE:
<223> OTHER INFORMATION: ebv-miR-BART8-3p (antisense)

<400> SEQUENCE: 48
ucuacgaccc cauagauugu gac                                         23

<210> SEQ ID NO 49
<211> LENGTH: 22
<212> TYPE: RNA
<213> ORGANISM: Artificial Sequence
<220> FEATURE:
<223> OTHER INFORMATION: ebv-miR-BART9-5p (sense)

<400> SEQUENCE: 49
uacuggaccc ugaauuggaa ac                                          22

<210> SEQ ID NO 50
<211> LENGTH: 22
<212> TYPE: RNA
<213> ORGANISM: Artificial Sequence
<220> FEATURE:
<223> OTHER INFORMATION: ebv-miR-BART9-5p (antisense)

<400> SEQUENCE: 50
guuuccaauu caggguccag ua                                          22

<210> SEQ ID NO 51
<211> LENGTH: 23
<212> TYPE: RNA
<213> ORGANISM: Artificial Sequence
<220> FEATURE:
<223> OTHER INFORMATION: ebv-miR-BART9-3p (sense)

<400> SEQUENCE: 51
uaacacuuca uggguccgu agu                                          23

<210> SEQ ID NO 52
```

```
<211> LENGTH: 23
<212> TYPE: RNA
<213> ORGANISM: Artificial Sequence
<220> FEATURE:
<223> OTHER INFORMATION: ebv-miR-BART9-3p (antisense)

<400> SEQUENCE: 52
acuacgggac ccaugaagug uua                                       23

<210> SEQ ID NO 53
<211> LENGTH: 22
<212> TYPE: RNA
<213> ORGANISM: Artificial Sequence
<220> FEATURE:
<223> OTHER INFORMATION: ebv-miR-BART22-5p (sense)

<400> SEQUENCE: 53
ugcuagaccc uggaguugaa cc                                        22

<210> SEQ ID NO 54
<211> LENGTH: 22
<212> TYPE: RNA
<213> ORGANISM: Artificial Sequence
<220> FEATURE:
<223> OTHER INFORMATION: ebv-miR-BART22-5p (antisense)

<400> SEQUENCE: 54
gguucaacuc cagggucuag ca                                        22

<210> SEQ ID NO 55
<211> LENGTH: 23
<212> TYPE: RNA
<213> ORGANISM: Artificial Sequence
<220> FEATURE:
<223> OTHER INFORMATION: ebv-miR-BART22-3p (sense)

<400> SEQUENCE: 55
uuacaaaguc auggucuagu agu                                       23

<210> SEQ ID NO 56
<211> LENGTH: 23
<212> TYPE: RNA
<213> ORGANISM: Artificial Sequence
<220> FEATURE:
<223> OTHER INFORMATION: ebv-miR-BART22-3p (antisense)

<400> SEQUENCE: 56
acuacuagac caugacuuug uaa                                       23

<210> SEQ ID NO 57
<211> LENGTH: 22
<212> TYPE: RNA
<213> ORGANISM: Artificial Sequence
<220> FEATURE:
<223> OTHER INFORMATION: ebv-miR-BART10-5p (sense)

<400> SEQUENCE: 57
gccaccucuu ugguucugua ca                                        22

<210> SEQ ID NO 58
<211> LENGTH: 22
<212> TYPE: RNA
<213> ORGANISM: Artificial Sequence
<220> FEATURE:
<223> OTHER INFORMATION: ebv-miR-BART10-5p (antisense)

<400> SEQUENCE: 58
```

```
uguacagaac caaagagguq gc                                              22

<210> SEQ ID NO 59
<211> LENGTH: 23
<212> TYPE: RNA
<213> ORGANISM: Artificial Sequence
<220> FEATURE:
<223> OTHER INFORMATION: ebv-miR-BART10-3p (sense)

<400> SEQUENCE: 59
uacauaacca uggaguuggc ugu                                             23

<210> SEQ ID NO 60
<211> LENGTH: 23
<212> TYPE: RNA
<213> ORGANISM: Artificial Sequence
<220> FEATURE:
<223> OTHER INFORMATION: ebv-miR-BART10-3p (antisense)

<400> SEQUENCE: 60
acagccaacu ccaugguuau gua                                             23

<210> SEQ ID NO 61
<211> LENGTH: 24
<212> TYPE: RNA
<213> ORGANISM: Artificial Sequence
<220> FEATURE:
<223> OTHER INFORMATION: ebv-miR-BART11-5p (sense)

<400> SEQUENCE: 61
ucagacaguu uggugcgcua guug                                            24

<210> SEQ ID NO 62
<211> LENGTH: 24
<212> TYPE: RNA
<213> ORGANISM: Artificial Sequence
<220> FEATURE:
<223> OTHER INFORMATION: ebv-miR-BART11-5p (antisense)

<400> SEQUENCE: 62
caacuagcgc accaaacugu cuga                                            24

<210> SEQ ID NO 63
<211> LENGTH: 21
<212> TYPE: RNA
<213> ORGANISM: Artificial Sequence
<220> FEATURE:
<223> OTHER INFORMATION: ebv-miR-BART11-3p (sense)

<400> SEQUENCE: 63
acgcacacca ggcugacugc c                                               21

<210> SEQ ID NO 64
<211> LENGTH: 21
<212> TYPE: RNA
<213> ORGANISM: Artificial Sequence
<220> FEATURE:
<223> OTHER INFORMATION: ebv-miR-BART11-3p (antisense)

<400> SEQUENCE: 64
ggcagucagc cuggugugcg u                                               21

<210> SEQ ID NO 65
<211> LENGTH: 21
<212> TYPE: RNA
```

<213> ORGANISM: Artificial Sequence
<220> FEATURE:
<223> OTHER INFORMATION: ebv-miR-BART12-5p (sense)

<400> SEQUENCE: 65
acccgcccau caccaccgga c                                      21

<210> SEQ ID NO 66
<211> LENGTH: 21
<212> TYPE: RNA
<213> ORGANISM: Artificial Sequence
<220> FEATURE:
<223> OTHER INFORMATION: ebv-miR-BART12-5p (antisense)

<400> SEQUENCE: 66
guccgguggu gaugggcggg u                                      21

<210> SEQ ID NO 67
<211> LENGTH: 22
<212> TYPE: RNA
<213> ORGANISM: Artificial Sequence
<220> FEATURE:
<223> OTHER INFORMATION: ebv-miR-BART12-3p (sense)

<400> SEQUENCE: 67
uccuguggug uuuggugugg uu                                     22

<210> SEQ ID NO 68
<211> LENGTH: 22
<212> TYPE: RNA
<213> ORGANISM: Artificial Sequence
<220> FEATURE:
<223> OTHER INFORMATION: ebv-miR-BART12-3p (antisense)

<400> SEQUENCE: 68
aaccacacca aacaccacag ga                                     22

<210> SEQ ID NO 69
<211> LENGTH: 23
<212> TYPE: RNA
<213> ORGANISM: Artificial Sequence
<220> FEATURE:
<223> OTHER INFORMATION: ebv-miR-BART19-5p (sense)

<400> SEQUENCE: 69
acauuccccg caaacaugac aug                                    23

<210> SEQ ID NO 70
<211> LENGTH: 23
<212> TYPE: RNA
<213> ORGANISM: Artificial Sequence
<220> FEATURE:
<223> OTHER INFORMATION: ebv-miR-BART19-5p (antisense)

<400> SEQUENCE: 70
caugucaugu uugcggggaa ugu                                    23

<210> SEQ ID NO 71
<211> LENGTH: 21
<212> TYPE: RNA
<213> ORGANISM: Artificial Sequence
<220> FEATURE:
<223> OTHER INFORMATION: ebv-miR-BART19-3p (sense)

<400> SEQUENCE: 71
uuuuguuugc uugggaaugc u                                      21

<210> SEQ ID NO 72
<211> LENGTH: 21
<212> TYPE: RNA
<213> ORGANISM: Artificial Sequence
<220> FEATURE:
<223> OTHER INFORMATION: ebv-miR-BART19-3p (antisense)

<400> SEQUENCE: 72
agcauuccca agcaaacaaa a                                          21

<210> SEQ ID NO 73
<211> LENGTH: 21
<212> TYPE: RNA
<213> ORGANISM: Artificial Sequence
<220> FEATURE:
<223> OTHER INFORMATION: ebv-miR-BART20-5p (sense)

<400> SEQUENCE: 73
uagcaggcau gcuucauuc c                                           21

<210> SEQ ID NO 74
<211> LENGTH: 21
<212> TYPE: RNA
<213> ORGANISM: Artificial Sequence
<220> FEATURE:
<223> OTHER INFORMATION: ebv-miR-BART20-5p (antisense)

<400> SEQUENCE: 74
ggaaugaaga caugccugcu a                                          21

<210> SEQ ID NO 75
<211> LENGTH: 22
<212> TYPE: RNA
<213> ORGANISM: Artificial Sequence
<220> FEATURE:
<223> OTHER INFORMATION: ebv-miR-BART20-3p (sense)

<400> SEQUENCE: 75
caugaaggca cagccuguua cc                                         22

<210> SEQ ID NO 76
<211> LENGTH: 22
<212> TYPE: RNA
<213> ORGANISM: Artificial Sequence
<220> FEATURE:
<223> OTHER INFORMATION: ebv-miR-BART20-3p (antisense)

<400> SEQUENCE: 76
gguaacaggc ugugccuuca ug                                         22

<210> SEQ ID NO 77
<211> LENGTH: 22
<212> TYPE: RNA
<213> ORGANISM: Artificial Sequence
<220> FEATURE:
<223> OTHER INFORMATION: ebv-miR-BART13-5p (sense)

<400> SEQUENCE: 77
aaccggcucg uggcucguac ag                                         22

<210> SEQ ID NO 78
<211> LENGTH: 22
<212> TYPE: RNA
<213> ORGANISM: Artificial Sequence
<220> FEATURE:

<223> OTHER INFORMATION: ebv-miR-BART13-5p (antisense)

<400> SEQUENCE: 78
cuguacgagc cacgagccgg uu                                            22

<210> SEQ ID NO 79
<211> LENGTH: 23
<212> TYPE: RNA
<213> ORGANISM: Artificial Sequence
<220> FEATURE:
<223> OTHER INFORMATION: ebv-miR-BART13-3p (sense)

<400> SEQUENCE: 79
uguaacuugc cagggacggc uga                                           23

<210> SEQ ID NO 80
<211> LENGTH: 23
<212> TYPE: RNA
<213> ORGANISM: Artificial Sequence
<220> FEATURE:
<223> OTHER INFORMATION: ebv-miR-BART13-3p (antisense)

<400> SEQUENCE: 80
ucagccgucc cuggcaaguu aca                                           23

<210> SEQ ID NO 81
<211> LENGTH: 22
<212> TYPE: RNA
<213> ORGANISM: Artificial Sequence
<220> FEATURE:
<223> OTHER INFORMATION: ebv-miR-BART14-5p (sense)

<400> SEQUENCE: 81
uacccuacgc ugccgauuua ca                                            22

<210> SEQ ID NO 82
<211> LENGTH: 22
<212> TYPE: RNA
<213> ORGANISM: Artificial Sequence
<220> FEATURE:
<223> OTHER INFORMATION: ebv-miR-BART14-5p (antisense)

<400> SEQUENCE: 82
uguaaaucgg cagcguaggg ua                                            22

<210> SEQ ID NO 83
<211> LENGTH: 22
<212> TYPE: RNA
<213> ORGANISM: Artificial Sequence
<220> FEATURE:
<223> OTHER INFORMATION: ebv-miR-BART14-3p (sense)

<400> SEQUENCE: 83
uaaaugcugc aguaguaggg au                                            22

<210> SEQ ID NO 84
<211> LENGTH: 22
<212> TYPE: RNA
<213> ORGANISM: Artificial Sequence
<220> FEATURE:
<223> OTHER INFORMATION: ebv-miR-BART14-3p (antisense)

<400> SEQUENCE: 84
aucccuacua cugcagcauu ua                                            22

```
<210> SEQ ID NO 85
<211> LENGTH: 22
<212> TYPE: RNA
<213> ORGANISM: Artificial Sequence
<220> FEATURE:
<223> OTHER INFORMATION: ebv-miR-BART2-5p (sense)

<400> SEQUENCE: 85
uauuuucugc auucgcccuu gc                                             22

<210> SEQ ID NO 86
<211> LENGTH: 22
<212> TYPE: RNA
<213> ORGANISM: Artificial Sequence
<220> FEATURE:
<223> OTHER INFORMATION: ebv-miR-BART2-5p (antisense)

<400> SEQUENCE: 86
gcaagggcga augcagaaaa ua                                             22

<210> SEQ ID NO 87
<211> LENGTH: 24
<212> TYPE: RNA
<213> ORGANISM: Artificial Sequence
<220> FEATURE:
<223> OTHER INFORMATION: ebv-miR-BART2-3p (sense)

<400> SEQUENCE: 87
aaggagcgau uuggagaaaa uaaa                                           24

<210> SEQ ID NO 88
<211> LENGTH: 24
<212> TYPE: RNA
<213> ORGANISM: Artificial Sequence
<220> FEATURE:
<223> OTHER INFORMATION: ebv-miR-BART2-3p (antisense)

<400> SEQUENCE: 88
uuuauuuucu ccaaaucgcu ccuu                                           24
```

COMPOSITION FOR PROMOTING APOPTOSIS OR INHIBITING CELL GROWTH, COMPRISING EPSTEIN-BARR VIRUS MICRORNA

CROSS REFERENCE TO RELATED APPLICATIONS

This application is the national stage of International Application No. PCT/KR2012/004149, filed May 24, 2012, entitled, "Composition For Promoting Apoptosis Or Inhibiting Cell Growth, Comprising Epstein-Barr Virus Microrna," which claims the benefit of priority of Korean Patent Application No. 10-2011-0049812, filed May 25, 2011, the contents of both of which are incorporated herein by reference in their entirety.

TECHNICAL FIELD

Disclosed is use of an miRNA of an Epstein-Barr virus (EBV), more specifically, miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, miR-BART2-3p, and a mimic thereof for promoting apoptosis or inhibiting cell growth.

A study for the present invention was supported by grants from the Gyeonggi Regional Research Centre (GRRC) of the Catholic University of Korea [(GRRC Catholic 2010-A01). RNA-based development of biopharmaceutical lead molecules] and from the National R&D Program for Cancer Control, Ministry for Health, Welfare and Family affairs, Republic of Korea (0920210).

BACKGROUND ART

Apoptosis is an important process in normal development and functioning of multicellular organisms. Physiological apoptosis plays an important role in various normal processes, however, abnormal apoptosis causes various diseases (Science. 267, 1456-1462 (1995); Biochem Biophys Res Commun. 266 (3), 699-717 (1999)).

For example, inhibited apoptosis may cause a cancer, an autoimmune disease, an inflammatory disease, and a virus infection. On the other hand, excessive apoptosis may cause a degenerative neurologic disease or a cardiac disease. Thus, as regulation of apoptosis in a concerned tissue or cell is very valuable, a substance promoting apoptosis is useful for preventing and treating an autoimmune disease, a lymphoproliferative disease, an inflammatory disease, and a virus infection and a substance inhibiting apoptosis is useful for preventing and treating a degenerative neurologic disease or a cardiac disease.

MicroRNAs (miRNAs) are non-coding RNAs formed when a long hairpin type transcript produced in a cell is cleaved by enzymes named as Drosha and Dicer into 19 to 25 nt. miRNAs have a base sequence which is incompletely complementary to a 3' untranslated region of a target gene mRNA, and thus inhibit translation. However, miRNAs have a fully complementary base sequence, and thus induce mRNA degradation.

In 2004, a first case of a virus that EBV expresses its own viral miRNA was reported. Afterwards, 25 pre-miRNAs were discovered. Among the pre-miRNAs, 22 pre-miRNAs produced from a BART transcript were largely divided into Cluster 1 and Cluster 2, and were expressed in most of the EBV-related tumor or cell strain.

miR-BART5-5p, which is expressed in a EBV-infected cell, was reported to inhibit expression of PUMA, which is a pro-apoptotic protein, to increase a rate of cell survival rate (J Exp Med. 205(11), 2551-2560 (2008)). On the other hand, it was reported that, while LMP1, which is an oncogenic EBV protein, induces cell growth and transformation at a low LMP1 expression level, LMP1 inhibits cell growth at a high LMP1 expression level, and miR-BART1-5p, 16-5p, and 17-5p inhibit an LMP1 expression to decrease apoptosis (Proc Natl Acad Sci USA. 104(41), 16164-16169 (2007)). It was reported that miR-BART22-3p inhibits expression of LMP2A, which is known to be necessary to maintain EBV latency, and, although miR-BART22-3p does not affect cell growth or apoptosis, miR-BART22-3p may promote immune evasion (Neoplasia. 11(11), 1174-1184 (2009)). It was reported that miR-BART2-5p targets BALF5, which is an EBV DNA polymerase, to contribute to maintenance of EBV latency and, at the same time, targets MICB, which is a ligand of a natural killer cell, to evade an immune response by the natural killer cell (Nucleic Acids Res. 36(2), 666-675 (2008); Cell Host Microbe. 5(4), 376-385 (2009)). It was reported that miR-BART6-5p targets Dicer, which is related with miRNA biogenesis, and contributes to maintenance of EBV latency (*J Biol. Chem.* 285(43), 33358-33370 (2010)). Recently, it was proved through a luciferase reporter assay that miRNAs of BART Cluster 1 and Cluster 2 inhibit expression of Bim, which is a pro-apoptotic gene, and reduce apoptosis, but the specific BART miRNA having such functions was not identified (*Virology.* 412(2), 392-400 (2011)). As described above, EBV BART miRNAs are known to promote cell growth and inhibit apoptosis.

DETAILED DESCRIPTION OF THE INVENTION

Technical Problem

The present invention provides finding a substance promoting apoptosis and inhibiting cell growth and a method of using the substance.

Technical Solution

According to an aspect of the present invention, there is provided a use of EBV miRNA, more specifically, miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, miR-BART2-3p, and mimics thereof for promoting apoptosis or inhibiting cell growth.

The inventors of the present invention synthesized and prepared mimics of BART miRNAs in a form of a double stranded RNA and investigated the effects by transfecting the mimics of BART miRNAs to AGS, which is a tumor cell strain not infected with EBV. As a result, it was unexpectedly shown that the mimics of miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, and miR-BART2-3p inhibit cell growth and promote apoptosis. In addition, the apoptosis promoting effect of the BART miRNA mimics showed a synergic effect when 5-FU, which is an anticancer agent, was simultaneously administered.

In addition, in order to investigate an apoptosis mechanism of miR-BART15-3p, which is a representative example of the BART miRNAs and mimics thereof having an effect of promoting apoptosis, the inventors of the present invention selected an expected target gene of miR-BART15-3p and tested the expected target gene. A decrease of BIRC6 protein level and a decrease of mRNA level of TAX1BP1 by miR-BART15-3p were verified by Western blotting and QRT-PCR, respectively, indicating that BIRC6 and TAX1BP were the target genes.

The mimics of EBV BART miRNA used in the experiments are shown below.

TABLE 1

| miRNA Name | | Duplex Sequence |
|---|---|---|
| ebv-miR-BART3-5p | sense | 5'ACCUAGUGUUAGUGUUGUGCU 3' (SEQ NO: 1) |
| ebv-miR-BART3-5p | antisense | 5'AGCACAACACUAACACUAGGU 3' (SEQ NO: 2) |
| ebv-miR-BART3-3p | sense | 5'CGCACCACUAGUCACCAGGUGU 3' (SEQ NO: 3) |
| ebv-miR-BART3-3p | antisense | 5'ACACCUGGUGACUAGUGGUGCG 3' (SEQ NO: 4) |
| ebv-miR-BART4-5p | sense | 5'GACCUGAUGCUGCUGGUGUGCU 3' (SEQ NO: 5) |
| ebv-miR-BART4-5p | antisense | 5'AGCACACCAGCAGCAUCAGGUC 3' (SEQ NO: 6) |
| ebv-miR-BART4-3p | sense | 5'CACAUCACGUAGGCACCAGGUGU 3' (SEQ NO: 7) |
| ebv-miR-BART4-3p | antisense | 5'ACACCUGGUGCCUACGUGAUGUG 3' (SEQ NO: 8) |
| ebv-miR-BART1-5p | sense | 5'UCUUAGUGGAAGUGACGUGCUGUG 3' (SEQ NO: 9) |
| ebv-miR-BART1-5p | antisense | 5'CACAGCACGUCACUUCCACUAAGA3' (SEQ NO: 10) |
| ebv-miR-BART1-3p | sense | 5'UAGCACCGCUAUCCACUAUGUC 3' (SEQ NO: 11) |
| ebv-miR-BART1-3p | antisense | 5'GACAUAGUGGAUAGCGGUGCUA 3' (SEQ NO: 12) |
| ebv-miR-BART15-5p | sense | 5'AGGGAAACAUGACCACCUGAAGUC3' (SEQ NO: 13) |
| ebv-miR-BART15-5p | antisense | 5GACUUCAGGUGGUCAUGUUUCCCU 3' (SEQ NO: 14) |
| ebv-miR-BART15-3p | sense | 5'GUCAGUGGUUUUGUUUCCUUGA 3' (SEQ NO: 15) |
| ebv-miR-BART15-3p | antisense | 5'UCAAGGAAACAAAACCACUGAC 3' (SEQ NO: 16) |
| ebv-miR-BART5-5p | sense | 5'CAAGGUGAAUAUAGCUGCCCAUCG 3' (SEQ NO: 17) |
| ebv-miR-BART5-5p | antisense | 5'CGAUGGGCAGCUAUAUUCACCUUG 3' (SEQ NO: 18) |
| ebv-miR-BART5-3p | sense | 5'GUGGGCCGCUGUUCACCU3' (SEQ NO: 19) |
| ebv-miR-BART5-3p | antisense | 5'AGGUGAACAGCGGCCCAC 3' (SEQ NO: 20) |

TABLE 1-continued

| miRNA Name | | Duplex Sequence |
|---|---|---|
| ebv-miR-BART16-5p | sense | 5'UUAGAUAGAGUGGGUGUGUGCUCU 3' (SEQ NO: 21) |
| ebv-miR-BART16-5p | antisense | 5'AGAGCACACACCCACUCUAUCUAA 3' (SEQ NO: 22) |
| ebv-miR-BART16-3p | sense | 5'AUCACCACCCUCUAUCCAUAU 3' (SEQ NO: 23) |
| ebv-miR-BART16-3p | antisense | 5'AUAUGGAUAGAGGGUGGUGAU 3' (SEQ NO: 24) |
| ebv-miR-BART17-5p | sense | 5'UAAGAGGACGCAGGCAUACAAG 3' (SEQ NO: 25) |
| ebv-miR-BART17-5p | antisense | 5'CUUGUAUGCCUGCGUCCUCUUA 3' (SEQ NO: 26) |
| ebv-miR-BART17-3p | sense | 5'UGUAUGCCUGGUGUCCCCUUAGU 3' (SEQ NO: 27) |
| ebv-miR-BART17-3p | antisense | 5'ACUAAGGGGACACCAGGCAUACA 3' (SEQ NO: 28) |
| ebv-miR-BART6-5p | sense | 5'UAAGGUUGGUCCAAUCCAUAGG 3 (SEQ NO: 29) |
| ebv-miR-BART6-5p | antisense | 5'CCUAUGGAUUGGACCAACCUUA 3' (SEQ NO: 30) |
| ebv-miR-BART6-3p | sense | 5'CGGGGAUCGGACUAGCCUUAGA 3' (SEQ NO: 31) |
| ebv-miR-BART6-3p | antisense | 5'UCUAAGGCUAGUCCGAUCCCCG 3' (SEQ NO: 32) |

Sense and Antisense Sequences of Cluster 1 BART miRNA Mimics

TABLE 2

| miRNA Name | | Duplex Sequence |
|---|---|---|
| ebv-miR-BART21-5p | Sense | 5'UCACUAGUGAAGGCAACUAAC3' (SEQ NO: 33) |
| | Antisense | 5'GUUAGUUGCCUUCACUAGUGA3' (SEQ NO: 34) |
| ebv-miR-BART21-3p | Sense | 5'CUAGUUGUGCCCACUGGUGUUU3' (SEQ NO: 35) |
| | Antisense | 5'AAACACCAGUGGGCACAACUAG3' (SEQ NO: 36) |
| ebv-miR-BART18-5p | Sense | 5'UCAAGUUCGCACUUCCUAUACA3' (SEQ NO: 37) |
| | Antisense | 5'UGUAUAGGAAGUGCGAACUUGA3' (SEQ NO: 38) |
| ebv-miR-BART18-3p | Sense | 5'UAUCGGAAGUUUGGGCUUCGUC3' (SEQ NO: 39) |
| | Antisense | 5'GACGAAGCCCAAACUUCCGAUA3' (SEQ NO: 40) |
| ebv-miR-BART7-5p | Sense | 5'CCUGGACCUUGACUAUGAAACA3' (SEQ NO: 41) |
| | Antisense | 5'UGUUUCAUAGUCAAGGUCCAGG3' (SEQ NO: 42) |
| ebv-miR-BART7-3p | Sense | 5'CAUCAUAGUCCAGUGUCCAGGG3' (SEQ NO: 43) |

TABLE 2-continued

| | | |
|---|---|---|
| | Antisense | 5'CCCUGGACACUGGACUAUGAUG3' (SEQ NO: 44) |
| ebv-miR-BART8-5p | Sense | 5'UACGGUUUCCUAGAUUGUACAG3' (SEQ NO: 45) |
| | Antisense | 5'CUGUACAAUCUAGGAAACCGUA3' (SEQ NO: 46) |
| ebv-miR-BART8-3p | Sense | 5'GUCACAAUCUAUGGGGUCGUAGA3' (SEQ NO: 47) |
| | Antisense | 5'UCUACGACCCCAUAGAUUGUGAC3' (SEQ NO: 48) |
| ebv-miR-BART9-5p | Sense | 5'UACUGGACCCUGAAUUGGAAAC3' (SEQ NO: 49) |
| | Antisense | 5'GUUUCCAAUUCAGGGUCCAGUA3' (SEQ NO: 50) |
| ebv-miR-BART9-3p | Sense | 5'UAACACUUCAUGGGUCCCGUAGU3' (SEQ NO: 51) |
| | Antisense | 5'ACUACGGGACCCAUGAAGUGUUA3' (SEQ NO: 52) |
| ebv-miR-BART22-5p | Sense | 5'UGCUAGACCCUGGAGUUGAACC3' (SEQ NO: 53) |
| | Antisense | 5'GGUUCAACUCCAGGGUCUAGCA3' (SEQ NO: 54) |
| ebv-miR-BART22-3p | Sense | 5'UUACAAAGUCAUGGUCUAGUAGU3' (SEQ NO: 55) |
| | Antisense | 5'ACUACUAGACCAUGACUUUGUAA3' (SEQ NO: 56) |
| ebv-miR-BART10-5p | Sense | 5'GCCACCUCUUUGGUUCUGUACA3' (SEQ NO: 57) |
| | Antisense | 5'UGUACAGAACCAAAGAGGUGGC3' (SEQ NO: 58) |
| ebv-miR-BART10-3p | Sense | 5'UACAUAACCAUGGAGUUGGCUGU3' (SEQ NO: 59) |
| | Antisense | 5'ACAGCCAACUCCAUGGUUAUGUA3' (SEQ NO: 60) |
| ebv-miR-BART11-5p | Sense | 5'UCAGACAGUUUGGUGCGCUAGUUG3' (SEQ NO: 61) |
| | Antisense | 5'CAACUAGCGCACCAAACUGUCUGA3' (SEQ NO: 62) |
| ebv-miR-BART11-5p | Sense | 5'ACGCACACCAGGCUGACUGCC3' (SEQ NO: 63) |
| | Antisense | 5'GGCAGUCAGCCUGGUGUGCGU3' (SEQ NO: 64) |
| ebv-miR-BART12-5p | Sense | 5'ACCCGCCCAUCACCACCGGAC3' (SEQ NO: 65) |
| | Antisense | 5'GUCCGGUGGUGAUGGGCGGGU3' (SEQ NO: 66) |
| ebv-miR-BART12-3p | Sense | 5'UCCUGUGGUGUUUGGUGUGGGUU3' (SEQ NO: 67) |
| | Antisense | 5'AACCACACCAAACACCACAGGA3' (SEQ NO: 68) |
| ebv-miR-BART19-5p | Sense | 5'ACAUUCCCCGCAAACAUGACAUG3' (SEQ NO: 69) |
| | Antisense | 5'CAUGUCAUGUUUGCGGGGAAUGU3' (SEQ NO: 70) |
| ebv-miR-BART19-3p | Sense | 5'UUUUGUUUGCUUGGGAAUGCU3' (SEQ NO: 71) |
| | Antisense | 5'AGCAUUCCCAAGCAAACAAAA3' (SEQ NO: 72) |
| ebv-miR-BART20-5p | Sense | 5'UAGCAGGCAUGUCUUCAUUCC3' (SEQ NO: 73) |
| | Antisense | 5'GGAAUGAAGACAUGCCUGCUA3' (SEQ NO: 74) |
| ebv-miR-BART20-3p | Sense | 5'CAUGAAGGCACAGCCUGUUACC3' (SEQ NO: 75) |
| | Antisense | 5'GGUAACAGGCUGUGCCUUCAUG3' (SEQ NO: 76) |
| ebv-miR-BART13-5p | Sense | 5'AACCGGCUCGUGGCUCGUACAG3' (SEQ NO: 77) |
| | Antisense | 5'CUGUACGAGCCACGAGCCGGUU3' (SEQ NO: 78) |
| ebv-miR-BART13-3p | Sense | 5'UGUAACUUGCCAGGGACGGCUGA3' (SEQ NO: 79) |
| | Antisense | 5'UCAGCCGUCCCUGGCAAGUUACA3' (SEQ NO: 80) |
| ebv-miR-BART14-5p | Sense | 5'UACCCUACGCUGCCGAUUUACA3' (SEQ NO: 81) |
| | Antisense | 5'UGUAAAUCGGCAGCGUAGGGUA3' (SEQ NO: 82) |
| ebv-miR-BART14-3p | Sense | 5'UAAAUGCUGCAGUAGUAGGGAU3' (SEQ NO: 83) |
| | Antisense | 5'AUCCCUACUACUGCAGCAUUUA3' (SEQ NO: 84) |
| ebv-miR-BART2-5p | Sense | 5'UAUUUUCUGCAUUCGCCCUUGC3' (SEQ NO: 85) |
| | Antisense | 5'GCAAGGGCGAAUGCAGAAAAUA3' (SEQ NO: 86) |
| ebv-miR-BART2-3p | Sense | 5'AAGGAGCGAUUUGGAGAAAAUAAA3' (SEQ NO: 87) |
| | Antisense | 5'UUUAUUUUCUCCAAAUCGCUCCUU3' (SEQ NO: 88) |

Sense and Antisense Sequences of Cluster 2 BART miRNA Mimics

Hereinafter, the present invention is described in more detail.

Unless otherwise defined, all technical terms used herein have the same meaning as commonly understood by one of ordinary skill in the art to which this invention belongs.

An embodiment of the present invention is a pharmaceutical composition, which is for preventing or treating a disease related to decreased apoptosis or abnormal cell growth, comprising at least one selected from the group consisting of miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, and miR-BART2-3p of EBV and a pharmaceutically acceptable carriers. Another embodiment of the present invention is a pharmaceutical composition, which is for preventing or treating a disease related to decreased apoptosis or abnormal cell growth, comprising at least one selected from the group consisting of an miR-BART4-5p mimic, miR-BART4-3p mimic, miR-BART1-5p mimic, miR-BART15-3p mimic, miR-BART5-5p mimic, miR-BART5-3p mimic, miR-BART16-5p mimic, miR-BART16-3p mimic, miR-BART17-3p mimic, miR-BART21-3p mimic, miR-BART18-5p mimic, miR-BART7-5p mimic, miR-BART9-5p mimic, miR-BART22-5p mimic, miR-BART20-3p mimic, miR-BART13-5p mimic, miR-BART13-3p mimic, and miR-BART2-3p mimic of EBV and a pharmaceutically acceptable carriers.

The structure of BART miRNAs or miR-BART mimics used in various embodiments of the present invention may have either a blunt end or a cohesive end as long as the end allows for inhibiting expression of a target gene by an effect of RNAi. The cohesive end structure may have a 3'-end overhang structure or a 5'-end overhang structure. The number of overhang nucleotides is not limited but, it may be, for example, one to eight, or appropriately, one to four. The BART miRNAs or miR-BART mimics used in various embodiments of the present invention may be chemically modified by a general method known in this art to prevent rapid degradation by an in vivo nuclease and increase in vivo stability. For example, a hydroxyl group at a 2'-position of a ribose ring may be modified with H, OR, R, R'OR, SH, SR, NH2, NHR, NR2, N3, CN, F, Cl, Br, or I (Herein, R may be an alkyl or aryl, or appropriately, a C1 to C6 alkyl group and R' may be an alkylene, or appropriately, a C1 to C6 alkylene.), or an phosphate backbone may be modified with phosphorothioate, phosphorodithioate, alkyl phosphonate, phosphoramidate, or boranophosphate. In addition, BART miRNAs or mimics of miRNAs may be used by substituting at least one site of the sequences of the BART miRNAs or mimics of miRNAs with a locked nucleic acid (LNA), a peptide nucleic acid (PNA) or a morpholino, which is a nucleic acid analog, to prevent a rapid in vivo degradation and increase stability of the BART miRNAs or mimics of miRNAs. The BART miRNAs or miR-BART mimics used in various embodiments of the present invention include a variant, which is a functional equivalent including a change which does not decrease activity of BART miRNAs or miR-BART mimics, having at least one of substitution, addition, deletion and their combination of the BART miRNAs or miR-BART mimics.

The BART miRNAs or miR-BART mimics used in various embodiments of the present invention may have a complete type in which two RNA strands as a pair form a double-strand RNA, which is a type formed as an miRNA is directly synthesized in vitro and then introduced to a cell through transfection, or a type which is formed by a modification to a structure having a short hairpin which may be used for transfection by a plasmid pre-miRNA vector and a PCR-induced miRNA expression cassette.

The BART miRNAs or miR-BART mimics used in various embodiments of the present invention may be prepared by various synthesis methods known in this art including a direct chemical synthesis method (Sui G et al., Proc Natl Acad Sci USA 99:5515-5520, 2002), a synthesis method using in vitro transcription (Brummelkamp T R et al., Science. 296:550-553, 2002), and a method of cleaving a long double-strand RNA, which is synthesized by in vitro transcription, with an RNase III family enzyme (Paul C P et al., Nature Biotechnology 20:505-508, 2002).

The BART miRNAs or miR-BART mimics used in various embodiments of the present invention may be included as composites with various nucleic acid vectors (viral or nonviral vectors) known in this art in order to increase intracellular transfer efficiency. For example, the BART miRNAs or miR-BART mimics may be included as a recombinant plasmid or virus vector expressing the BART miRNAs or miR-BART mimics. Plasmids which may be used for this purpose are pSilencer (Ambion), pSiEx (Novagen), siXpress (Takara Bio), pBLOCK-iT™ (Invitrogen), pcDNA3.1 (Invitrogen), pCEP4 (Invitrogen), and SilenCircle™ (Allele), but are not limited thereto. Viral vectors which may be used to include the BART miRNAs or miR-BART mimics are a retroviral vector, an adenovirus vector, an adeno-associated virus vector, a vaccinia virus vector, a lentivirus vector, a herpes virus vector, an alpha-viral vector, an EB virus vector, a papilloma virus vector, and a foamy virus vector, but are not limited thereto. In addition, nonviral vectors which may be used to include the BART miRNAs or miR-BART mimics are, as a carrier reagent, Mirus TrasIT-TKO lipophilic reagent, lipofectin, lipofectamine, cellfectin, G-fectin, a cationic phospholipid nanoparticle, a cationic polymer, a cationic micelle, a cationic emulsion or liposome, a ligand-DNA complex, and a gene gun, but are not limited thereto. A nonviral vector as a liposome is an amphipathic agent, for example, a lipid existing as a micelle, an insoluble single layer, or a lamella layer in liquid crystal or an aqueous solution. Lipids for preparing a liposome include a monoglyceride, a diglyceride, a sulfatide, a lysolecithin, a lechitin phospholipod, aponin, bile acid, and lipofectin, but are not limited thereto.

In addition, to increase in vivo stability of the BART miRNAs or miR-BART mimics, the BART miRNAs or miR-BART mimics may be prepared as a pharmaceutical preparation by using general intracellular RNA transfer techniques known in this art such as a method of increasing intracellular absorption by coupling a biocompatible polymer such as polyethylene glycol. The intracellular RNA transfer techniques include a method of making a cell suspension by electroporation in a solution including an miRNA or a mimic thereof to introduce the miRNA or the mimic thereof to the cell by applying a high voltage DC pulse to the solution. By an in vivo method, a solution including an miRNA or a mimic thereof may be injected into a part of a body and a DC voltage may be applied as a pulse through an electrode to introduce the miRNA or the mimic thereof to a cell.

As the mimics used in various embodiments of the present invention, an miR-BART4-5p mimic to which an RNA having a sequence of SEQ NO:5 and an RNA having a sequence of SEQ NO:6 are hybridized, an miR-BART4-3p to which an RNA having a sequence of SEQ NO:7 and an RNA having a sequence of SEQ NO:8 are hybridized, an miR-BART1-5p to which an RNA having a sequence of SEQ NO:9 and an RNA having a sequence of SEQ NO:10 are hybridized, an miR-BART15-3p mimic to which an RNA having a sequence of SEQ NO:15 and an RNA having a sequence of SEQ NO:16 are hybridized, an miR-BART5-5p mimic to which an RNA having a sequence of SEQ NO:17 and an RNA having a sequence of SEQ NO:18 are hybridized, an miR-BART5-3p mimic to which an RNA having a sequence of SEQ NO:19 and an RNA having a sequence of SEQ NO:20 are hybridized, an miR-BART16-5p mimic to which an RNA having a sequence of SEQ NO:21 and an RNA having a sequence of SEQ NO:22 are hybridized, an miR-BART16-3p mimic to which an RNA having a sequence of SEQ NO:23 and an RNA having a sequence of SEQ NO:24 are hybridized, an miR-BART17-3p mimic to which an RNA having a sequence of SEQ NO:27 and an RNA having a sequence of SEQ NO:28 are hybridized, an miR-BART21-3p mimic to which an RNA having a sequence of SEQ NO:35 and an RNA having a sequence of SEQ NO:36 are hybridized, an miR-BART18-5p mimic to which an RNA having a sequence of SEQ NO:37 and an RNA having a sequence of SEQ NO:38 are hybridized, an miR-BART7-5p mimic to which an RNA having a sequence of SEQ NO:41 and an RNA having a sequence of SEQ NO:42 are hybridized, an miR-BART9-5p mimic to which an RNA having a sequence of SEQ NO:49 and an RNA having a sequence of SEQ NO:50 are hybridized, an miR-BART22-5p mimic to which an RNA having a sequence of SEQ NO:53 and an RNA having a sequence of SEQ NO:54 are hybridized, an miR-BART20-3p mimic to which an RNA having a sequence of SEQ NO:75 and an RNA having a sequence of SEQ NO:76 are hybridized, an miR-BART13-5p mimic to which an RNA having a sequence of SEQ NO:77 and an RNA having a sequence of SEQ NO:78 are hybridized, an miR-BART13-3p mimic to which an RNA having a sequence of SEQ NO:79 and an RNA having a sequence of SEQ NO:80 are hybridized, and an miR-BART2-3p to which an RNA having a sequence of SEQ NO:87 and an RNA having a sequence of SEQ NO:88 are hybridized may be used.

Another embodiment of the present invention is a method of preventing or treating a disease related to decreased apoptosis or abnormal cell growth by using at least one selected from the group consisting of EBV miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, and miR-BART2-3p.

Another embodiment of the present invention is a method of preventing or treating a disease related to decreased apoptosis or abnormal cell growth by using at least one selected from the group consisting of an miR-BART4-5p mimic, an miR-BART4-3p mimic, an miR-BART1-5p mimic, an miR-BART15-3p mimic, an miR-BART5-5p mimic, an miR-BART5-3p mimic, an miR-BART16-5p mimic, an miR-BART16-3p mimic, an miR-BART17-3p mimic, an miR-BART21-3p mimic, an miR-BART18-5p mimic, an miR-BART7-5p mimic, an miR-BART9-5p mimic, an miR-BART22-5p mimic, an miR-BART20-3p mimic, an miR-BART13-5p mimic, an miR-BART13-3p mimic, and an miR-BART2-3p of EBV. As the mimics used in various embodiments of the present invention, an miR-BART4-5p mimic to which an RNA having a sequence of SEQ NO:5 and an RNA having a sequence of SEQ NO:6 are hybridized, an miR-BART4-3p to which an RNA having a sequence of SEQ NO:7 and an RNA having a sequence of SEQ NO:8 are hybridized, an miR-BART1-5p to which an RNA having a sequence of SEQ NO:9 and an RNA having a sequence of SEQ NO:10 are hybridized, an miR-BART15-3p mimic to which an RNA having a sequence of SEQ NO:15 and an RNA having a sequence of SEQ NO:16 are hybridized, an miR-BART5-5p mimic to which an RNA having a sequence of SEQ NO:17 and an RNA having a sequence of SEQ NO:18 are hybridized, an miR-BART5-3p mimic to which an RNA having a sequence of SEQ NO:19 and an RNA having a sequence of SEQ NO:20 are hybridized, an miR-BART16-5p mimic to which an RNA having a sequence of SEQ NO:21 and an RNA having a sequence of SEQ NO:22 are hybridized, an miR-BART16-3p mimic to which an RNA having a sequence of SEQ NO:23 and an RNA having a sequence of SEQ NO:24 are hybridized, an miR-BART17-3p mimic to which an RNA having a sequence of SEQ NO:27 and an RNA having a sequence of SEQ NO:28 are hybridized, an miR-BART21-3p mimic to which an RNA having a sequence of SEQ NO:35 and an RNA having a sequence of SEQ NO:36 are hybridized, an miR-BART18-5p mimic to which an RNA having a sequence of SEQ NO:37 and an RNA having a sequence of SEQ NO:38 are hybridized, an miR-BART7-5p mimic to which an RNA having a sequence of SEQ NO:41 and an RNA having a sequence of SEQ NO:42 are hybridized, an miR-BART9-5p mimic to which an RNA having a sequence of SEQ NO:49 and an RNA having a sequence of SEQ NO:50 are hybridized, an miR-BART22-5p mimic to which an RNA having a sequence of SEQ NO:53 and an RNA having a sequence of SEQ NO:54 are hybridized, an miR-BART20-3p mimic to which an RNA having a sequence of SEQ NO:75 and an RNA having a sequence of SEQ NO:76 are hybridized, an miR-BART13-5p mimic to which an RNA having a sequence of SEQ NO:77 and an RNA having a sequence of SEQ NO:78 are hybridized, an miR-BART13-3p mimic to which an RNA having a sequence of SEQ NO:79 and an RNA having a sequence of SEQ NO:80 are hybridized, and an miR-BART2-3p to which an RNA having a sequence of SEQ NO:87 and an RNA having a sequence of SEQ NO:88 are hybridized may be used.

The diseases related to decreased apoptosis or abnormal cell growth are, for example, tumors, autoimmune diseases, lymphoproliferative diseases, inflammatory diseases, viral infections, restenosis of blood vessels by angioplasty, and fibrosis by overgrowth of fibroblasts, but are not limited thereto. The tumors include stomach cancer, bladder cancer, a brain tumor, breast cancer, bone cancer, cervical cancer, chronic lymphocytic leukemia, colorectal cancer, esophageal cancer, hepatocellular cancer, lymphoblastic leukemia, follicular lymphoma, T-cell or B-cell originated lymphoid malignancies, melanoma, myeloid leukemia, myeloma, oral cancer, ovarian cancer, non-small cell lung cancer, prostate cancer, spleen cancer, fibrosarcoma, myosarcoma, liposarcoma, chondrosarcoma, osteogenic sarcoma, chordoma, angiosarcoma, endotheliosarcoma, lymphangiosarcoma, lymphangioendothelioblastoma, synovioma, mesothelioma, an Ewing tumor, leiomyosarcoma, rhabdomyosarcoma, a colon tumor, colorectal cancer, pancreatic cancer, uterine cancer, head and neck cancer, skin cancer, a squamous cell tumor, a sebaceous gland tumor, a papillary tumor, papillary adenoma, cystadenocarcinoma, a medullary tumor, a bronchogenic tumor, a renal cell tumor, liver cancer, a bile gland tumor, choriocarcinoma, seminoma, fetal servant, a Wilm's tumor, testicular cancer, a lung tumor, a small cell lung tumor, a non-small cell lung tumor, a bladder tumor, epithelioma, neuroglioma, astrocytoma, medulloblastoma, craniopharyngioma, cerebral ventricle ependymoma, pinealocytoma, angioblastoma, a acoustic nerve tumor, oligodendrocyte, meningioma, neuroblastoma, retinoblastoma, leukemia, lymphoma, Kaposi sarcoma, and nasopharyngeal epithelial carcinoma, but are not limited thereto.

Another embodiment of the present invention is a composition, which is for promoting apoptosis or inhibiting cell growth, comprising at least one selected from the group consisting of EBV miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, and miR-BART2-3p.

Another embodiment of the present invention is a pharmaceutical composition, which is for promoting apoptosis or inhibiting cell growth, including at least one selected from the group consisting of an miR-BART4-5p mimic, an miR-BART4-3p mimic, an miR-BART1-5p mimic, an miR-BART15-3p mimic, an miR-BART5-5p mimic, an miR-BART5-3p mimic, an miR-BART16-5p mimic, an miR-BART16-3p mimic, an miR-BART17-3p mimic, an miR-BART21-3p mimic, an miR-BART18-5p mimic, an miR- BART7-5p mimic, an miR-BART9-5p mimic, an miR-BART22-5p mimic, an miR-BART20-3p mimic, an miR-BART13-5p mimic, an miR-BART13-3p mimic, and an miR-BART2-3p of EBV.

An Example of the present invention includes a composition, which is for promoting apoptosis or inhibiting cell growth, comprising at least one selected from the group consisting of an miR-BART4-5p mimic to which an RNA having a sequence of SEQ NO:5 and an RNA having a sequence of SEQ NO:6 are hybridized, an miR-BART4-3p to which an RNA having a sequence of SEQ NO:7 and an RNA having a sequence of SEQ NO:8 are hybridized, an miR-BART1-5p to which an RNA having a sequence of SEQ NO:9 and an RNA having a sequence of SEQ NO:10 are hybridized, an miR-BART15-3p mimic to which an RNA having a sequence of SEQ NO:15 and an RNA having a sequence of SEQ NO:16 are hybridized, an miR-BART5-5p mimic to which an RNA having a sequence of SEQ NO:17 and an RNA having a sequence of SEQ NO:18 are hybridized, an miR-BART5-3p mimic to which an RNA having a sequence of SEQ NO:19 and an RNA having a sequence of SEQ NO:20 are hybridized, an miR-BART16-5p mimic to which an RNA having a sequence of SEQ NO:21 and an RNA having a sequence of SEQ NO:22 are hybridized, an miR-BART16-3p mimic to which an RNA having a sequence of SEQ NO:23 and an RNA having a sequence of SEQ NO:24 are hybridized, an miR-BART17-3p mimic to which an RNA having a sequence of SEQ NO:27 and an RNA having a sequence of SEQ NO:28 are hybridized, an miR-BART21-3p mimic to which an RNA having a sequence of SEQ NO:35 and an RNA having a sequence of SEQ NO:36 are hybridized, an miR-BART18-5p mimic to which an RNA having a sequence of SEQ NO:37 and an RNA having a sequence of SEQ NO:38 are hybridized, an miR-BART7-5p mimic to which an RNA having a sequence of SEQ NO:41 and an RNA having a sequence of SEQ NO:42 are hybridized, an miR-BART9-5p mimic to which an RNA having a sequence of SEQ NO:49 and an RNA having a sequence of SEQ NO:50 are hybridized, an miR-BART22-5p mimic to which an RNA having a sequence of SEQ NO:53 and an RNA having a sequence of SEQ NO:54 are hybridized, an miR-BART20-3p mimic to which an RNA having a sequence of SEQ NO:75 and an RNA having a sequence of SEQ NO:76 are hybridized, an miR-BART13-5p mimic to which an RNA having a sequence of SEQ NO:77 and an RNA having a sequence of SEQ NO:78 are hybridized, an miR-BART13-3p mimic to which an RNA having a sequence of SEQ NO:79 and an RNA having a sequence of SEQ NO:80 are hybridized, and an miR-BART2-3p to which an RNA having a sequence of SEQ NO:87 and an RNA having a sequence of SEQ NO:88 are hybridized. The compositions of the present invention may be used in vivo or in vitro.

Another embodiment of the present invention is a method of promoting apoptosis or inhibiting cell growth by using at least one selected from the group consisting of EBV miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, and miR-BART2-3p.

Another embodiment of the present invention is a method of promoting apoptosis or inhibiting cell growth by using at least one selected from the group consisting of an miR-BART4-5p mimic, an miR-BART4-3p mimic, an miR-BART1-5p mimic, an miR-BART15-3p mimic, an miR-BART5-5p mimic, an miR-BART5-3p mimic, an miR-BART16-5p mimic, an miR-BART16-3p mimic, an miR-BART17-3p mimic, an miR-BART21-3p mimic, an miR-BART18-5p mimic, an miR-BART7-5p mimic, an miR-BART9-5p mimic, an miR-BART22-5p mimic, an miR-BART20-3p mimic, an miR-BART13-5p mimic, an miR-BART13-3p mimic, and an miR-BART2-3p of EBV. As the mimics, an miR-BART4-5p mimic to which an RNA having a sequence of SEQ NO:5 and an RNA having a sequence of SEQ NO:6 are hybridized, an miR-BART4-3p to which an RNA having a sequence of SEQ NO:7 and an RNA having a sequence of SEQ NO:8 are hybridized, an miR-BART1-5p to which an RNA having a sequence of SEQ NO:9 and an RNA having a sequence of SEQ NO:10 are hybridized, an miR-BART15-3p mimic to which an RNA having a sequence of SEQ NO:15 and an RNA having a sequence of SEQ NO:16 are hybridized, an miR-BART5-5p mimic to which an RNA having a sequence of SEQ NO:17 and an RNA having a sequence of SEQ NO:18 are hybridized, an miR-BART5-3p mimic to which an RNA having a sequence of SEQ NO:19 and an RNA having a sequence of SEQ NO:20 are hybridized, an miR-BART16-5p mimic to which an RNA having a sequence of SEQ NO:21 and an RNA having a sequence of SEQ NO:22 are hybridized, an miR-BART16-3p mimic to which an RNA having a sequence of SEQ NO:23 and an RNA having a sequence of SEQ NO:24 are hybridized, an miR-BART17-3p mimic to which an RNA having a sequence of SEQ NO:27 and an RNA having a sequence of SEQ NO:28 are hybridized, an miR-BART21-3p mimic to which an RNA having a sequence of SEQ NO:35 and an RNA having a sequence of SEQ NO:36 are hybridized, an miR-BART18-5p mimic to which an RNA having a sequence of SEQ NO:37 and an RNA having a sequence of SEQ NO:38 are hybridized, an miR-BART7-5p mimic to which an RNA having a sequence of SEQ NO:41 and an RNA having a sequence of SEQ NO:42 are hybridized, an miR-BART9-5p mimic to which an RNA having a sequence of SEQ NO:49 and an RNA having a sequence of SEQ NO:50 are hybridized, an miR-BART22-5p mimic to which an RNA having a sequence of SEQ NO:53 and an RNA having a sequence of SEQ NO:54 are hybridized, an miR-BART20-3p mimic to which an RNA having a sequence of SEQ NO:75 and an RNA having a sequence of SEQ NO:76 are hybridized, an miR-BART13-5p mimic to which an RNA having a sequence of SEQ NO:77 and an RNA having a sequence of SEQ NO:78 are hybridized, an miR-BART13-3p mimic to which an RNA having a sequence of SEQ NO:79 and an RNA having a sequence of SEQ NO:80 are hybridized, and an miR-BART2-3p to which an RNA having a sequence of SEQ NO:87 and an RNA having a sequence of SEQ NO:88 are hybridized may be used.

Another embodiment of the present invention is a kit, which is for promoting apoptosis or inhibiting cell growth, comprising at least one selected from the group consisting of EBV miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, and miR-BART2-3p.

Another embodiment of the present invention is a kit, which is for promoting apoptosis or inhibiting cell growth, comprising at least one selected from the group consisting of an miR-BART4-5p mimic, an miR-BART4-3p mimic, an miR-BART1-5p mimic, an miR-BART15-3p mimic, an miR-BART5-5p mimic, an miR-BART5-3p mimic, an miR-BART16-5p mimic, an miR-BART16-3p mimic, an miR-BART17-3p mimic, an miR-BART21-3p mimic, an miR-BART18-5p mimic, an miR-BART7-5p mimic, an miR- BART9-5p mimic, an miR-BART22-5p mimic, an miR-BART20-3p mimic, an miR-BART13-5p mimic, an miR-BART13-3p mimic, and an miR-BART2-3p of EBV. As the mimics, an miR-BART4-5p mimic to which an RNA having a sequence of SEQ NO:5 and an RNA having a sequence of SEQ NO:6 are hybridized, an miR-BART4-3p to which an RNA having a sequence of SEQ NO:7 and an RNA having a sequence of SEQ NO:8 are hybridized, an miR-BART1-5p to which an RNA having a sequence of SEQ NO:9 and an RNA having a sequence of SEQ NO:10 are hybridized, an miR-BART15-3p mimic to which an RNA having a sequence of SEQ NO:15 and an RNA having a sequence of SEQ NO:16 are hybridized, an miR-BART5-5p mimic to which an RNA having a sequence of SEQ NO:17 and an RNA having a sequence of SEQ NO:18 are hybridized, an miR-BART5-3p mimic to which an RNA having a sequence of SEQ NO:19 and an RNA having a sequence of SEQ NO:20 are hybridized, an miR-BART16-5p mimic to which an RNA having a sequence of SEQ NO:21 and an RNA having a sequence of SEQ NO:22 are hybridized, an miR-BART16-3p mimic to which an RNA having a sequence of SEQ NO:23 and an RNA having a sequence of SEQ NO:24 are hybridized, an miR-BART17-3p mimic to which an RNA having a sequence of SEQ NO:27 and an RNA having a sequence of SEQ NO:28 are hybridized, an miR-BART21-3p mimic to which an RNA having a sequence of SEQ NO:35 and an RNA having a sequence of SEQ NO:36 are hybridized, an miR-BART18-5p mimic to which an RNA having a sequence of SEQ NO:37 and an RNA having a sequence of SEQ NO:38 are hybridized, an miR-BART7-5p mimic to which an RNA having a sequence of SEQ NO:41 and an RNA having a sequence of SEQ NO:42 are hybridized, an miR-BART9-5p mimic to which an RNA having a sequence of SEQ NO:49 and an RNA having a sequence of SEQ NO:50 are hybridized, an miR-BART22-5p mimic to which an RNA having a sequence of SEQ NO:53 and an RNA having a sequence of SEQ NO:54 are hybridized, an miR-BART20-3p mimic to which an RNA having a sequence of SEQ NO:75 and an RNA having a sequence of SEQ NO:76 are hybridized, an miR-BART13-5p mimic to which an RNA having a sequence of SEQ NO:77 and an RNA having a sequence of SEQ NO:78 are hybridized, an miR-BART13-3p mimic to which an RNA having a sequence of SEQ NO:79 and an RNA having a sequence of SEQ NO:80 are hybridized, and an miR-BART2-3p to which an RNA having a sequence of SEQ NO:87 and an RNA having a sequence of SEQ NO:88 are hybridized may be used.

The kits may be used in vivo or in vitro to fulfill a purpose.

Another embodiment of the present invention may include at least one additional effective component in each of the embodiments of the present invention besides at least one selected from the group consisting of EBV miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, and miR-BART2-3p or at least one selected from the group consisting of an miR-BART4-5p mimic, an miR-BART4-3p mimic, an miR-BART1-5p mimic, an miR-BART15-3p mimic, an miR-BART5-5p mimic, an miR-BART5-3p mimic, an miR-BART16-5p mimic, an miR-BART16-3p mimic, an miR-BART17-3p mimic, an miR-BART21-3p mimic, an miR-BART18-5p mimic, an miR-BART7-5p mimic, an miR-BART9-5p mimic, an miR-BART22-5p mimic, an miR-BART20-3p mimic, an miR-BART13-5p mimic, an miR-BART13-3p mimic, and an miR-BART2-3p of EBV. The additional effective component may be administered in combination with another therapeutic mode which includes an anticancer agent, a chemotherapeutic agent, an immunotherapeutic agent, an antimicrobial agent, and an antivirus agent, but is not limited thereto, or may be administered in combination with radiation therapy or photodynamic therapy. The chemotherapeutic agent includes an antimetabolite agent, a DNA damaging agent, a microtube instabilizing agent, a microtube stabilizing agent, an actin depolymerizing agent, a growth inhibitor, a topoisomerase inhibitor, an HMG-CoA inhibitor, a purine inhibitor, a pyrimidine inhibitor, a metalloproteinase inhibitor, a CDK inhibitor, an angiogenesis inhibitor, a differentiation promoter, and an immunotherapy agent, but is not limited thereto.

Each of the embodiments of the present invention as described above may be applied to a human or an animal. A carrier included in the pharmaceutical composition of an embodiment of the present invention may be appropriately selected according to the administration route. In addition to the carrier, a diluent, a filler, a salt, a buffer, a stabilizer, a solubilizer or another substance known in this art may be used for the preparation of in the pharmaceutical composition.

An administration route of the pharmaceutical composition of an embodiment of the present invention includes parenteral, mucosal delivery, oral, sublingual, transdermal, topical, inhaled, intranasal, aerosol, intraocular, intravascular, endotracheal, intramuscular, intraperitoneal, intrarectal, intravaginal, a gene gun, a skin patch, an eye drop or mouthwash, and an injection, but is not limited thereto.

The quantity of miRNA or a mimic thereof included in the pharmaceutical composition of an embodiment of the present invention may be adjusted according to the characteristics of the disease to treat and severity thereof and characteristics of previous treatments given to a patient. An amount of from about 10 μg to about 20 mg per 1 kg of body weight or organ weight may be included in the pharmaceutical composition. In addition, the administration amount of the pharmaceutical composition is dependent upon an expression vector and a subject to be administered. For example, in a case of a viral vector, the amount of a recombinant virus including a viral vector is in the range from about $10^3$ to about $10^{12}$ pfu/kg.

Advantageous Effects

EBV miR-BART4-5p, miR-BART4-3p, miR-BART1-5p, miR-BART15-3p, miR-BART5-5p, miR-BART5-3p, miR-BART16-5p, miR-BART16-3p, miR-BART17-3p, miR-BART21-3p, miR-BART18-5p, miR-BART7-5p, miR-BART9-5p, miR-BART22-5p, miR-BART20-3p, miR-BART13-5p, miR-BART13-3p, and miR-BART2-3p or mimics thereof of the present invention have an effect of promoting apoptosis and inhibiting cell growth, and thus may be used as an active ingredient in a pharmaceutical composition for promoting apoptosis and inhibiting cell growth, a method of preventing or treating a disease related to decreased apoptosis or abnormal cell growth, and a pharmaceutical composition or a kit used in the method.

BEST MODE

Hereinafter, the embodiments of the present invention are described in detail with reference to Examples, but the embodiments of the present invention are not limited thereto.

EXAMPLE 1

Preparation of BART miRNA Mimics

Mature type BART miRNA mimics were synthesized by Genolution Pharmaceuticals (Seoul, Korea) according to our request and each sequence of the mimic is shown in Table 1 and Table 2.

EXAMPLE 2

Cell Culture and Transformation

An AGS cell strain (Korean Cell Line Bank), which is a stomach cancer cell strain, was cultured in an RPMI1640 (Gibco) culture medium including 10% fetal bovine serum. Mature type synthesized BART miRNAs were transfected to the AGS cell strain by using G-fectin (Genolution) according to a protocol of the manufacture.

EXAMPLE 3

Cell Growth Test (CCK-8 Assay)

To investigate the effect of individual EBV BART miRNAs on the AGS cell strain, the synthesized miRNAs were transfected to the AGS cell strain and, after 72 hours, cells were counted by CCK-8 assay. CCK-8 assay is an analytical method of counting cells by measuring colored formazans which are formed as tetrazolium salts are easily reduced by enzymes such as dehydrogenase included in a mitochondria.

Immediately after the AGS cell strain, which is an EBV-negative cell strain, was divided into 96-well plate having $1 \times 10^3$ cells/well, a synthesized miRNA (10 nM) was transfected by using G-fectin. After the transfection, according to the experimental objective, the cells were cultured at 37° C. in an incubator, and then CCK-8 was divided among the wells by allocating 10 μl of CCK-8 to each well and the resulting mixture was cultured in an incubator at 37° C. for two hours. Then, the light absorbance was measured with an ELISA measuring instrument.

Figure 1:
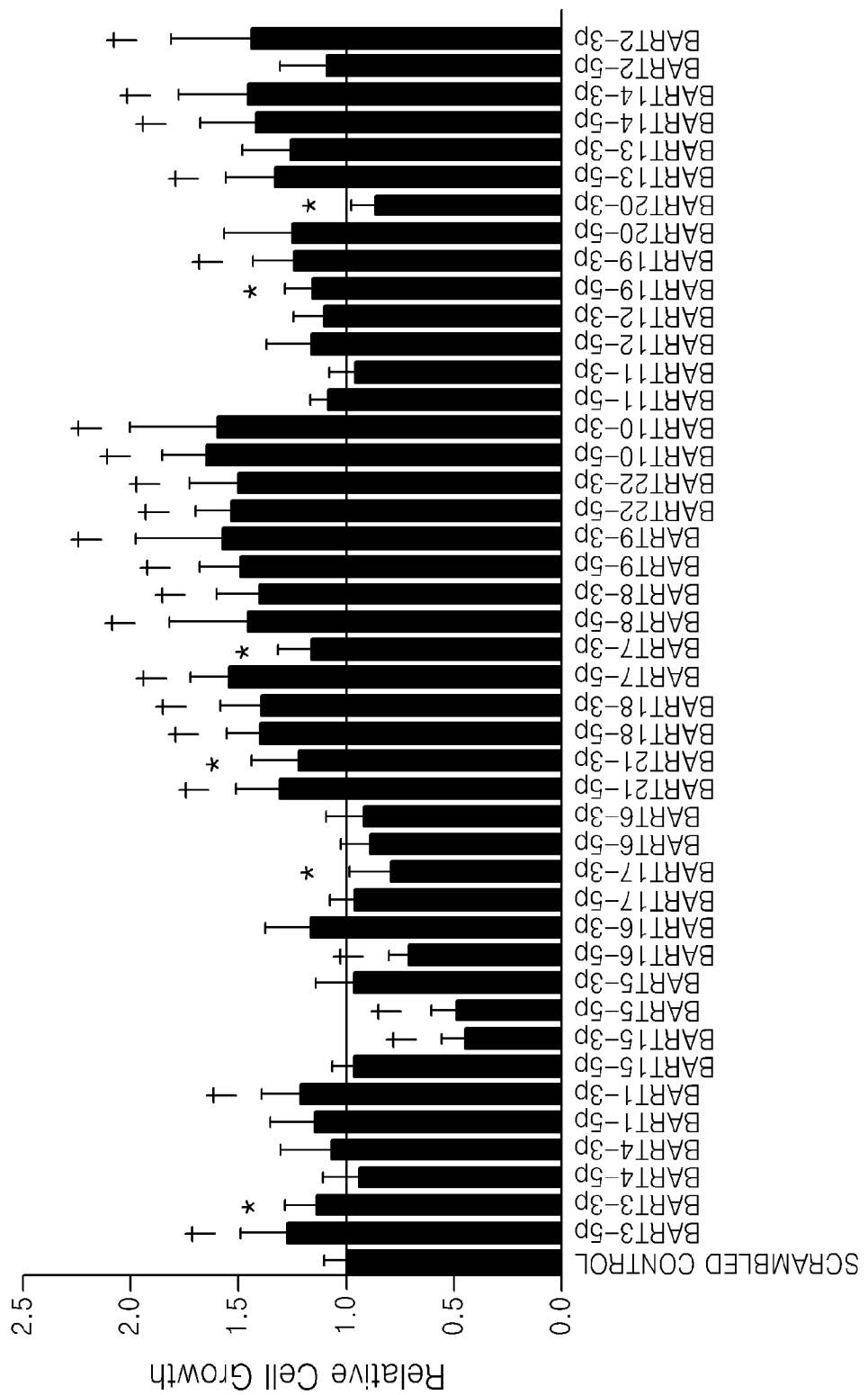
FIG. 1 shows the effect of individual EBV BART miRNA mimics on cell growth of an AGS cell strain. n=9 and * denotes P<0.05 and † denotes P<0.01.

Astonishingly, it was showing that mimics of miR-BART15-3p, miR-BART5-5p, miR-BART16-5p, miR-BART17-3p, and miR-BART20-3p inhibited cell growth (Table 3 and FIG. 1).

TABLE 3

|  | Relative Cell Growth | Standard Deviation | p value |
| --- | --- | --- | --- |
| Scrambled control | 1 | ±0.105353 |  |
| BART3-5p | 1.272325 | ±0.217357 | 0.00544481 |
| BART3-3p | 1.134944 | ±0.151438 | 0.04557112 |
| BART4-5p | 0.934781 | ±0.177295 | 0.36007269 |
| BART4-3p | 1.064824 | ±0.240507 | 0.47442005 |
| BART1-5p | 1.141337 | ±0.213522 | 0.10024868 |
| BART1-3p | 1.201069 | ±0.192482 | 0.01763492 |
| BART15-5p | 0.954474 | ±0.112565 | 0.38881645 |
| BART15-3p | 0.567640 | ±0.115939 | 1.0446E−08 |
| BART5-5p | 0.523116 | ±0.125143 | 5.8566E−08 |
| BART5-3p | 0.958293 | ±0.185292 | 0.56725316 |
| BART16-5p | 0.704990 | ±0.097954 | 1.3912E−05 |
| BART16-3p | 1.158869 | ±0.216577 | 0.07123824 |
| BART17-5p | 0.955098 | ±0.121512 | 0.41459821 |
| BART17-3p | 0.786497 | ±0.200822 | 0.01533499 |
| BART6-5p | 0.880951 | ±0.150107 | 0.07181715 |
| BART6-3p | 0.910063 | ±0.190801 | 0.23941914 |
| BART21-5p | 1.303997 | ±0.204928 | 0.00190053 |
| BART21-3p | 1.214906 | ±0.230037 | 0.02708391 |
| BART18-5p | 1.394629 | ±0.167148 | 4.5047E−05 |
| BART18-3p | 1.392545 | ±0.199891 | 0.00021762 |
| BART7-5p | 1.538728 | ±0.185522 | 4.0421E−06 |
| BART7-3p | 1.156463 | ±0.162895 | 0.02973117 |
| BART8-5p | 1.447761 | ±0.383293 | 0.00813662 |
| BART8-3p | 1.395663 | ±0.210488 | 0.00028794 |
| BART9-5p | 1.481661 | ±0.197746 | 3.1646E−05 |
| BART9-3p | 1.569261 | ±0.412069 | 0.00303969 |
| BART22-5p | 1.529268 | ±0.173392 | 2.8427E−06 |
| BART22-3p | 1.495125 | ±0.233896 | 0.000121 |
| BART10-5p | 1.646048 | ±0.208024 | 2.5367E−06 |
| BART10-3p | 1.591101 | ±0.414520 | 0.00097895 |
| BART11-5p | 1.079796 | ±0.086483 | 0.09942768 |
| BART11-3p | 0.945864 | ±0.134622 | 0.35714111 |
| BART12-5p | 1.158610 | ±0.214861 | 0.07006222 |
| BART12-3p | 1.102165 | ±0.143919 | 0.10628436 |
| BART19-5p | 1.151466 | ±0.136228 | 0.01861102 |

TABLE 3-continued

|  | Relative Cell Growth | Standard Deviation | p value |
|---|---|---|---|
| BART19-3p | 1.236815 | ±0.195064 | 0.00756775 |
| BART20-5p | 1.245400 | ±0.324239 | 0.0561646 |
| BART20-3p | 0.857667 | ±0.125343 | 0.01903579 |
| BART13-5p | 1.325692 | ±0.235629 | 0.0030181 |
| BART13-3p | 1.254611 | ±0.227980 | 0.01121857 |
| BART14-5p | 1.408238 | ±0.271466 | 0.00181178 |
| BART14-3p | 1.446585 | ±0.336094 | 0.00346446 |
| BART2-5p | 1.084926 | ±0.222797 | 0.3234295 |
| BART2-3p | 1.432948 | ±0.382729 | 0.00965267 |

EXAMPLE 4

Effect on Cell Growth Depending on Treatment Time

Figure 2:
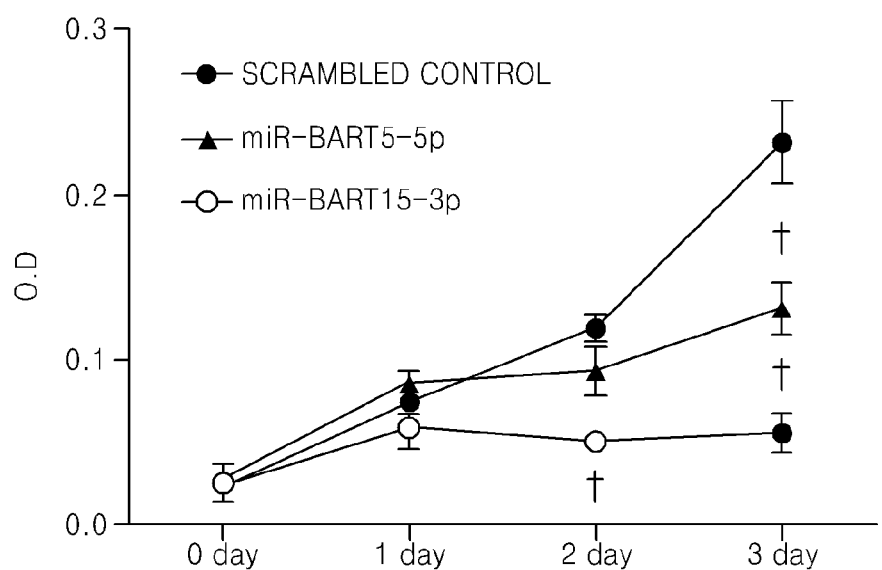
FIG. 2 shows the effect of miR-BART5-5p, miR-BART15-3p mimic on cell growth of an AGS cell strain depending on the treatment concentration. n=3, †:P<0.01.

By the method described in Example 3, miR-BART5-5p mimic or miR-BART15-3p mimic (10 nM) were transfected to the AGS cell strain, and the effect thereof on cell growth was investigated over time. Both of the EBV BART miRNAs greatly decreased cell growth and, particularly, the miR-BART15-3p mimic inhibited cell growth almost entirely (FIG. 2).

EXAMPLE 5

Figure 3:
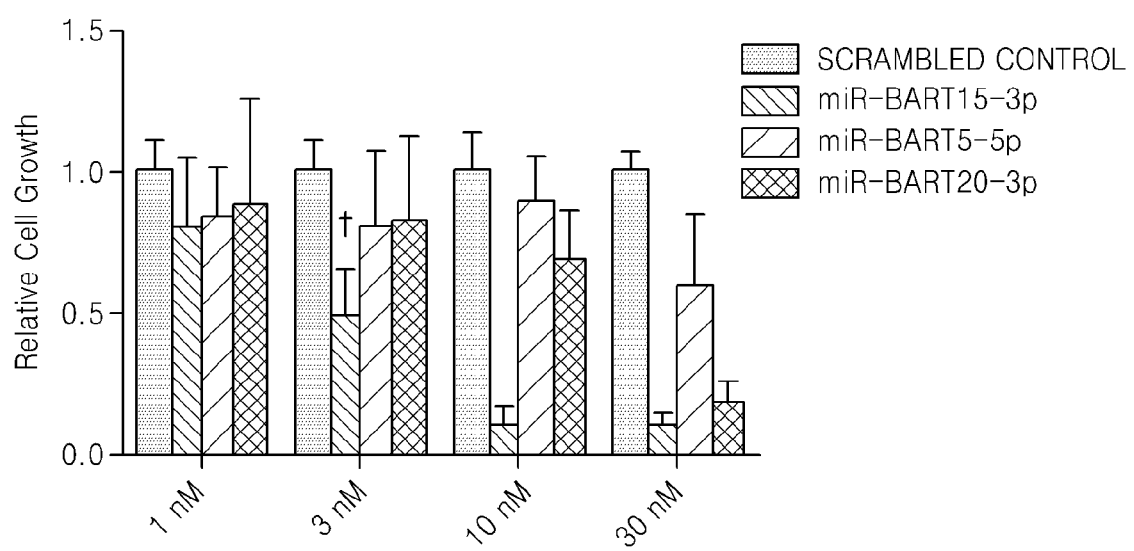
FIG. 3 shows the effect of miR-BART5-5p, miR-BART15-3p or miR-BART20-3p mimic on cell growth of an AGS cell strain depending on the treatment time. n=6, †:P<0.01.

Effect on Cell Growth Depending on Mimic Concentration miR-BART5-5p, miR-BART15-3p, and miR-BART20-3p were transfected to the AGS cell strain ($1 \times 10^3$ cells/well) in a concentration of 1, 3, 10, and 30 nM, and the effect on cell growth was investigated. Immediately after the AGS cell strain was divided into a 96-well plate such that $1 \times 10^3$ AGS cells were allocated to each well, a synthesized miRNA was transfected by using G-fectin. Seventy two hours after the transfection, CCK-8 was divided among the wells by allocating 10 μl of CCK-8 to each well, and the resulting mixture was cultured at 37° C. in an incubator for two hours. Then, the light absorbance was measured with an ELISA measuring instrument. miR-BART15-3p showed cell growth which was 50% lower than that of a scrambled control at 3 nM and almost no cell growth at 10 nM and 30 nM. miR-BART5-5p showed a tendency to inhibit cell growth beginning at 10 nM. miR-BART20-3p showed decreased cell growth, beginning at 10 nm, and almost no cell growth at 30 nm (FIG. 3).

EXAMPLE 6

Effect on Cell Cycle (Propidium Iodide Staining)

Effect of individual EBV BART miRNAs on cell cycle of the AGS cell strain was observed. The effect on cell cycle of an AGS cell strain was observed by PI staining when an miR-BART5-5p mimic or an miR-BART15-3p mimic was treated alone or treated in combination with 5-FU.

Figure 4:
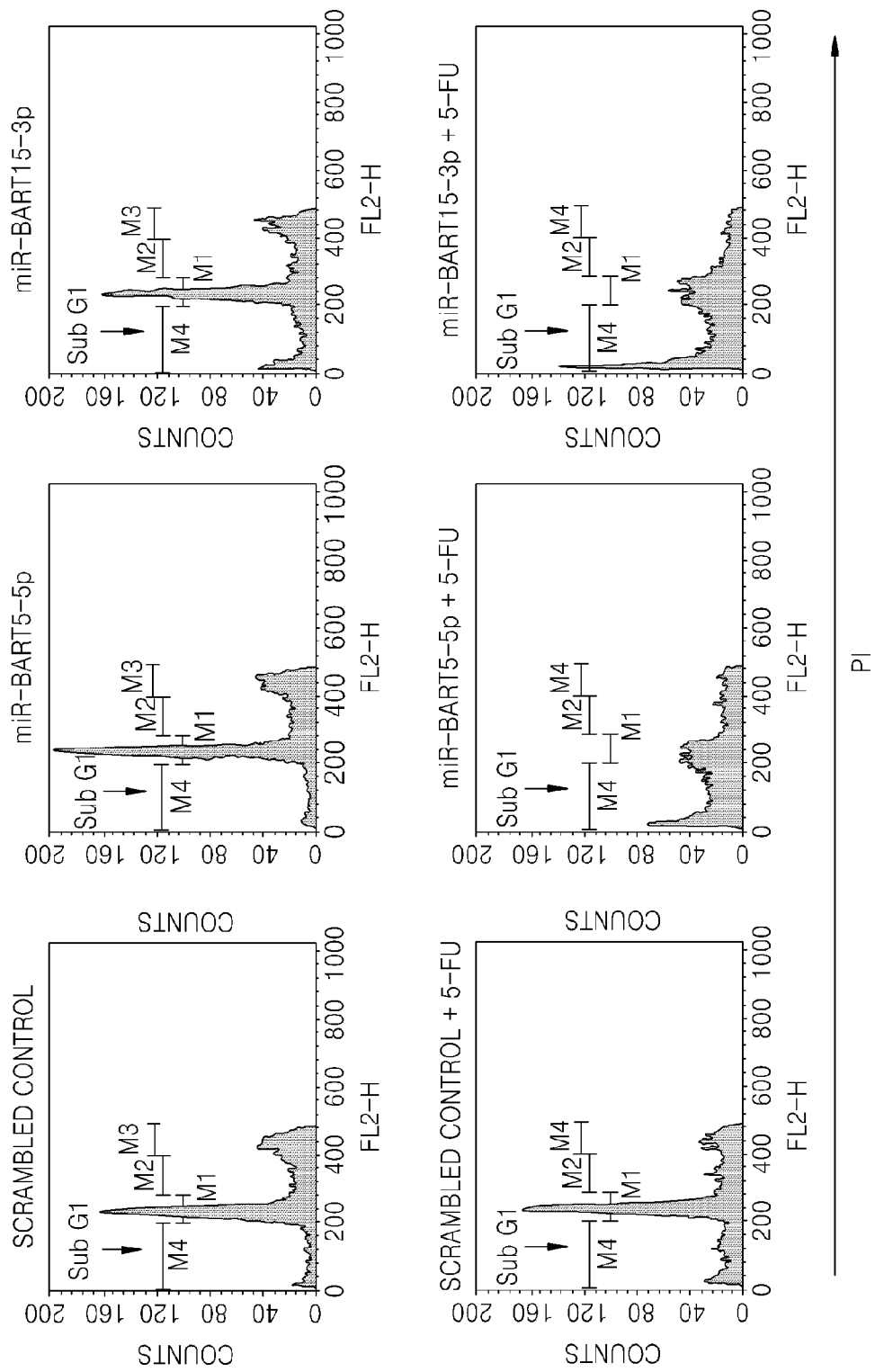
FIGS. 4 and 5 shows the effect on cell cycle of an AGS cell strain observed by PI staining when only an miR-BART5-5p mimic or an miR-BART15-3p mimic was treated and when miR-BART5-5p and miR-BART15-3p mimic were treated with 5-FU simultaneously. n=3, *:P<0.05, †:P<0.01.
Figure 5:
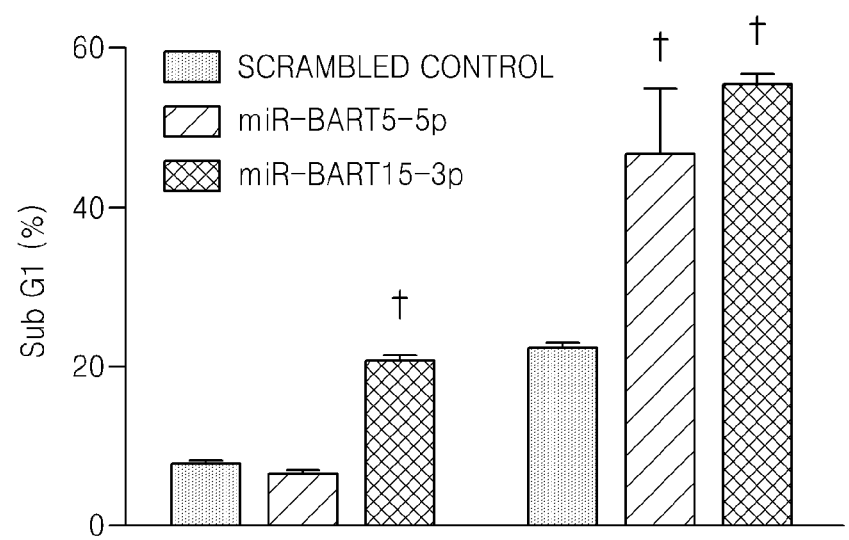

The AGS cells were divided into a 96-well plate such that $2 \times 10^5$ AGS cells were allocated to each well, and synthesized miRNAs (10 nM) were transfected and cultured at 37° C. in an incubator. Twenty four hours after the transfection, 10 uM of 5-FU, which is an anti-cancer agent, was treated in one case or not treated in another case, and then the resulting mixture was cultured in an incubator at 37° C. for 48 hours. The cells were detached by using Trypsin-EDTA and washed with PBS two times. Afterwards, the ratio of cells that had changed cell cycles to cells that did not have changed cell cycles was measured by FACS using propidium iodide staining (FIG. 4 and FIG. 5).

In the case of the AGS cells to which an miR-BAR15-3p mimic was transfected alone, the percentage of sub G1 was significantly higher than that of the scrambled control, indicating that apoptosis was promoted. In addition, in both of the miR-BART5-5p and miR-BART15-3p mimic, the ratio of sub G1, which is corresponding to an apoptosis cell, was greatly increased after the 5-FU treatment.

EXAMPLE 7

Effect of Combination Treatment with Anti-Cancer Agent on Cell Cycle

Immediately after the AGS cell strains, which are EBV-negative cell strains, were divided into a 6-well plate such that $2 \times 10^5$ AGS cells were allocated to each well, a synthesized miRNA (10 nM) was transfected by using G-fectin and cultured at 37° C. in an incubator. Twenty four hours after the transfection, 10 uM of 5-FU was treated and the resulting mixture was cultured at 37° C. in an incubator for 48 hours. The cells were detached by using Trypsin-EDTA and washed with PBS two times. Afterwards, DNA was stained by propidium iodide staining and the ratio of cells where cell cycle was changed was investigated by FACS.

Figure 6:
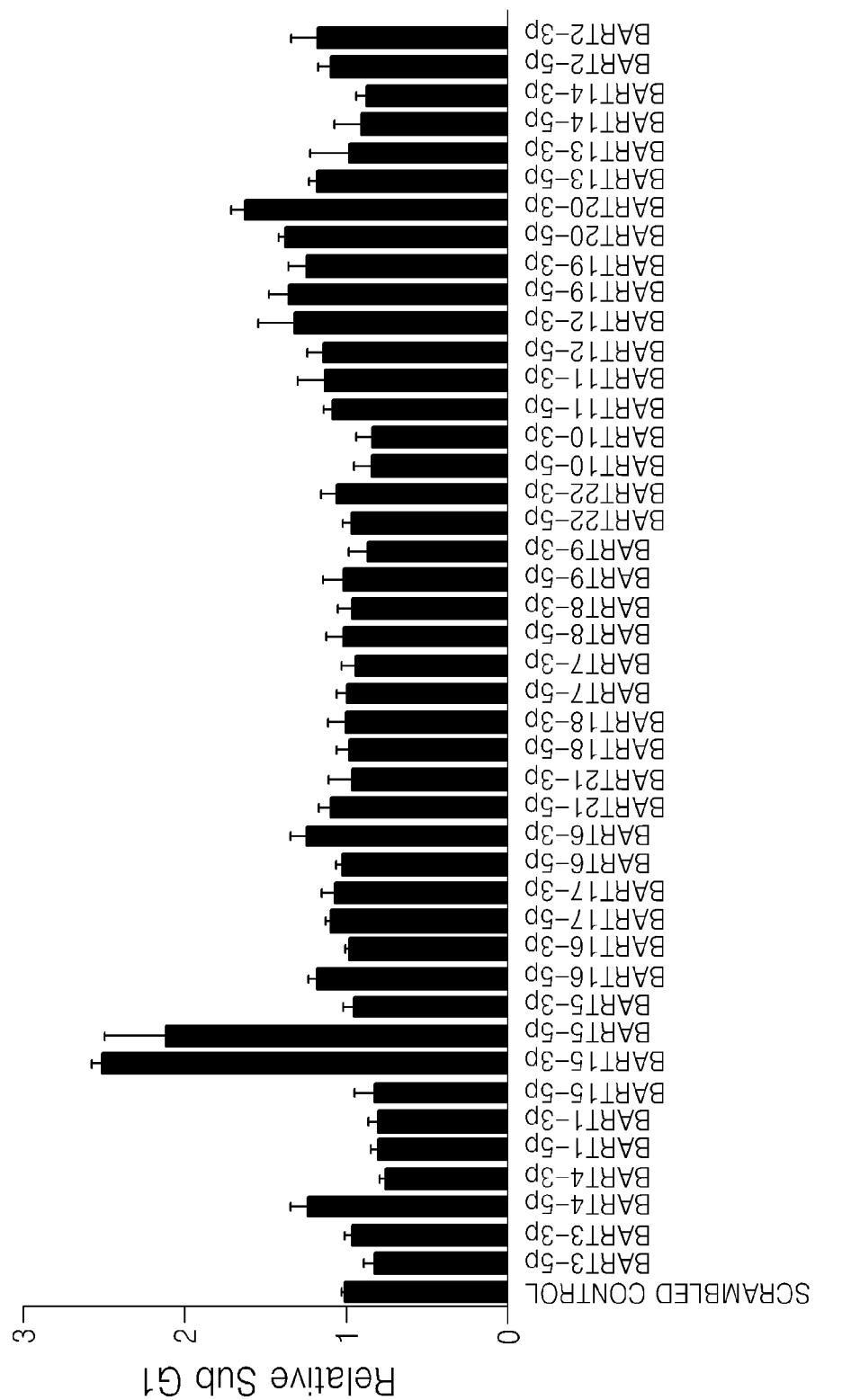
FIG. 6 shows the effect on cell cycle of an AGS cell strain observed by PI staining when a BART miRNA mimic was treated with 5-FU simultaneously. n=6, *:P<0.05, †, P<0.01.

The FACS measurement results showed that, when a mimic of miR-BART4-5p, 5-5p, 6-3p, 15-3p, 16-5p, 17-3p, 12-5p, 12-3p, 19-5p, 19-3p, 20-5p, 20-3p, 13-5p was treated, the ratio of sub G1 was increased, indicating that the apoptosis was increased (Table 4 and FIG. 6).

TABLE 4

|  | Relative Sub G1 | Stand. Dev. | p value |
|---|---|---|---|
| Scrambled control | 1 | ±0.031059 |  |
| BART3-5p | 0.822417 | ±0.067281 | 0.049080409 |
| BART3-3p | 0.964756 | ±0.047266 | 0.326058798 |
| BART4-5p | 1.235970 | ±0.118464 | 0.076996648 |
| BART4-3p | 0.754954 | ±0.049416 | 0.004307754 |
| BART1-5p | 0.802753 | ±0.046515 | 0.006954738 |
| BART1-3p | 0.794689 | ±0.070658 | 0.000329204 |
| BART15-5p | 0.819543 | ±0.131573 | 0.143851905 |
| BART15-3p | 2.507941 | ±0.074841 | 0.000890606 |
| BART5-5p | 2.111330 | ±0.385397 | 0.037943576 |
| BART5-3p | 0.948571 | ±0.075790 | 0.37614083 |
| BART16-5p | 1.181969 | ±0.053320 | 0.012037789 |
| BART16-3p | 0.985176 | ±0.019290 | 0.413525999 |
| BART17-5p | 1.098926 | ±0.033329 | 0.01271764 |
| BART17-3p | 1.067312 | ±0.086918 | 0.323110984 |
| BART6-5p | 1.022841 | ±0.042981 | 0.472476656 |
| BART6-3p | 1.239752 | ±0.103959 | 0.059670258 |
| BART21-5p | 1.086786 | ±0.090225 | 0.067468002 |
| BART21-3p | 0.964995 | ±0.143659 | 0.584959365 |
| BART18-5p | 0.982845 | ±0.079117 | 0.636157842 |
| BART18-3p | 0.996285 | ±0.119193 | 0.943515502 |
| BART7-5p | 0.991846 | ±0.075438 | 0.813623836 |
| BART7-3p | 0.939265 | ±0.094216 | 0.184372669 |
| BART8-5p | 1.012969 | ±0.113624 | 0.79643115 |
| BART8-3p | 0.961632 | ±0.091309 | 0.36746866 |
| BART9-5p | 1.005308 | ±0.138199 | 0.92984722 |
| BART9-3p | 0.866864 | ±0.113797 | 0.03265356 |
| BART22-5p | 0.965417 | ±0.051049 | 0.1940472 |
| BART22-3p | 1.053684 | ±0.103996 | 0.27121849 |
| BART10-5p | 0.833050 | ±0.118185 | 0.01548568 |
| BART10-3p | 0.839359 | ±0.092229 | 0.00677711 |
| BART11-5p | 1.081256 | ±0.064301 | 0.02701403 |

TABLE 4-continued

|  | Relative Sub G1 | Stand. Dev. | p value |
|---|---|---|---|
| BART11-3p | 1.127625 | ±0.175298 | 0.13865741 |
| BART12-5p | 1.134805 | ±0.103104 | 0.02204065 |
| BART12-3p | 1.316871 | ±0.233791 | 0.0216891 |
| BART19-5p | 1.348848 | ±0.126873 | 0.00060989 |
| BART19-3p | 1.243943 | ±0.119867 | 0.00292325 |
| BART20-5p | 1.378976 | ±0.042194 | 2.6358E-08 |
| BART20-3p | 1.618129 | ±0.09943 | 6.6505E-06 |
| BART13-5p | 1.178035 | ±0.055734 | 0.00013301 |
| BART13-3p | 0.981342 | ±0.246613 | 0.86134039 |
| BART14-5p | 0.907649 | ±0.168803 | 0.24466241 |
| BART14-3p | 0.875700 | ±0.061192 | 0.00301909 |
| BART2-5p | 1.092187 | ±0.086943 | 0.05007166 |
| BART2-3p | 1.178367 | ±0.170677 | 0.05327269 |

EXAMPLE 8

Measurement of Apoptosis (Annexin V Staining)

In the cases when an miR-BART5-5p mimic or an miR-BART15-3p mimic was treated alone or treated in combination with 5-FU, the effect thereof on apoptosis of the AGS cell strain was observed.

Immediately after the AGS cell strain, which is an EBV-negative cell strain, was divided was divided into a 6-well plate such that $2\times10^5$ AGS cells were allocated to each well, a synthesized miRNA (10 nM) was transfected by using G-fectin and the resulting mixture was cultured at 37 t in an incubatorTwenty four hours after the transfection, 10 uM of 5-FU was treated and the resulting mixture was cultured in an incubator at 37° C. for 48 hours. The cells were detached by using Trypsin-EDTA and washed with PBS two times. Afterwards, the cells were treated with a PE Annexin V Apoptosis Detection Kit and the changed ratio of apoptotic cell was investigated by FACS (FIG. 7).

Figure 7:
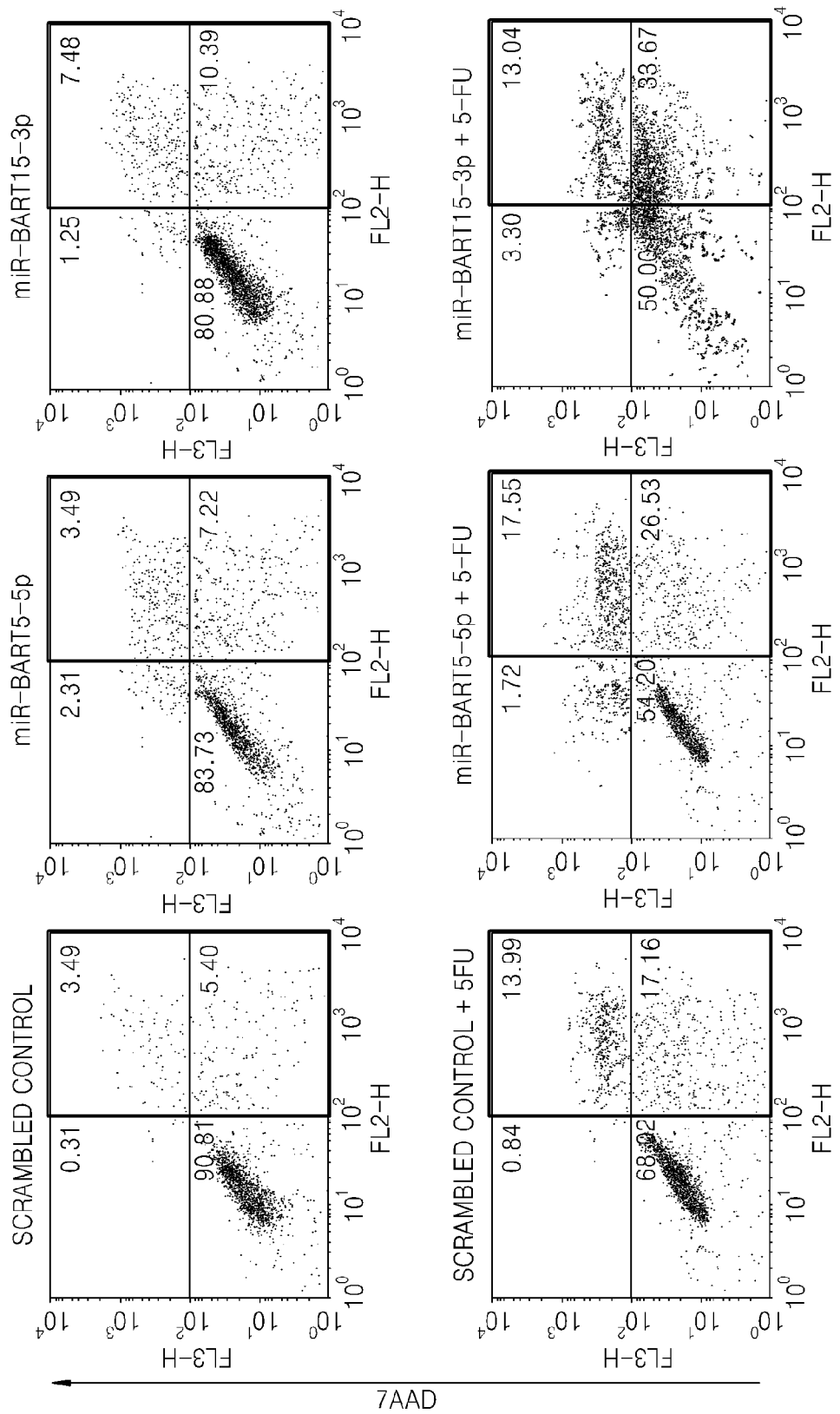
FIG. 7 shows the apoptosis effect investigated by Annexin V staining when only an miR-BART5-5p mimic or an miR-BART15-3p mimic was treated and when an miR-BART5-5p or an miR-BART15-3p mimic was treated with 5-FU simultaneously.

In both of the cases when an miR-BART5-5p mimic or an miR-BART15-3p mimic was treated alone and when miR-BART5-5p and miR-BART15-3p mimic were treated in combination with 5-FU, the ratio of the lower right in FIG. 7, which corresponds to early apoptotic cell, and the ratio of the upper right in FIG. 7, which corresponds to late apoptotic cell, were increased. Treatment of both of the two miR-BART5-5p and miR-BART15-3p mimics in combination with 5-FU showed a synergetic effect in view that the degree of apoptosis by the combination treatment was significantly greater than the sum of the degree of the apoptosis by the 5-FU treatment alone and the degree of the apoptosis by the apoptosis transfection of each miRNA mimic alone.

EXAMPLE 9

Effect of Combination Treatment with Anti-Cancer Agent on Apoptosis Inducement (Annexin V Staining)

Effect of individual EBV BART miRNAs on apoptosis of the AGS cell strain was observed by an Annexin V staining method.

Immediately after the AGS cell strain, which is an EBV-negative cell strain, is divided into a 6-well plate such that $2\times10^5$ AGS cells were allocated to each well, a synthesized miRNA (10 nM) was transfected by using G-fectin and the resulting mixture was cultured at 37° C. Twenty four hours after the transfection, 10 uM of 5-FU, which is an anti-cancer agent, was treated and the resulting mixture was cultured in an incubator at 37° C. for 48 hours. The cells were detached by using Trypsin-EDTA and washed with PBS two times. Afterwards, the cells were treated with a PE Annexin V Apoptosis Detection Kit and the ratio of cells where apoptosis took place was measured by FACS.

Figure 8:
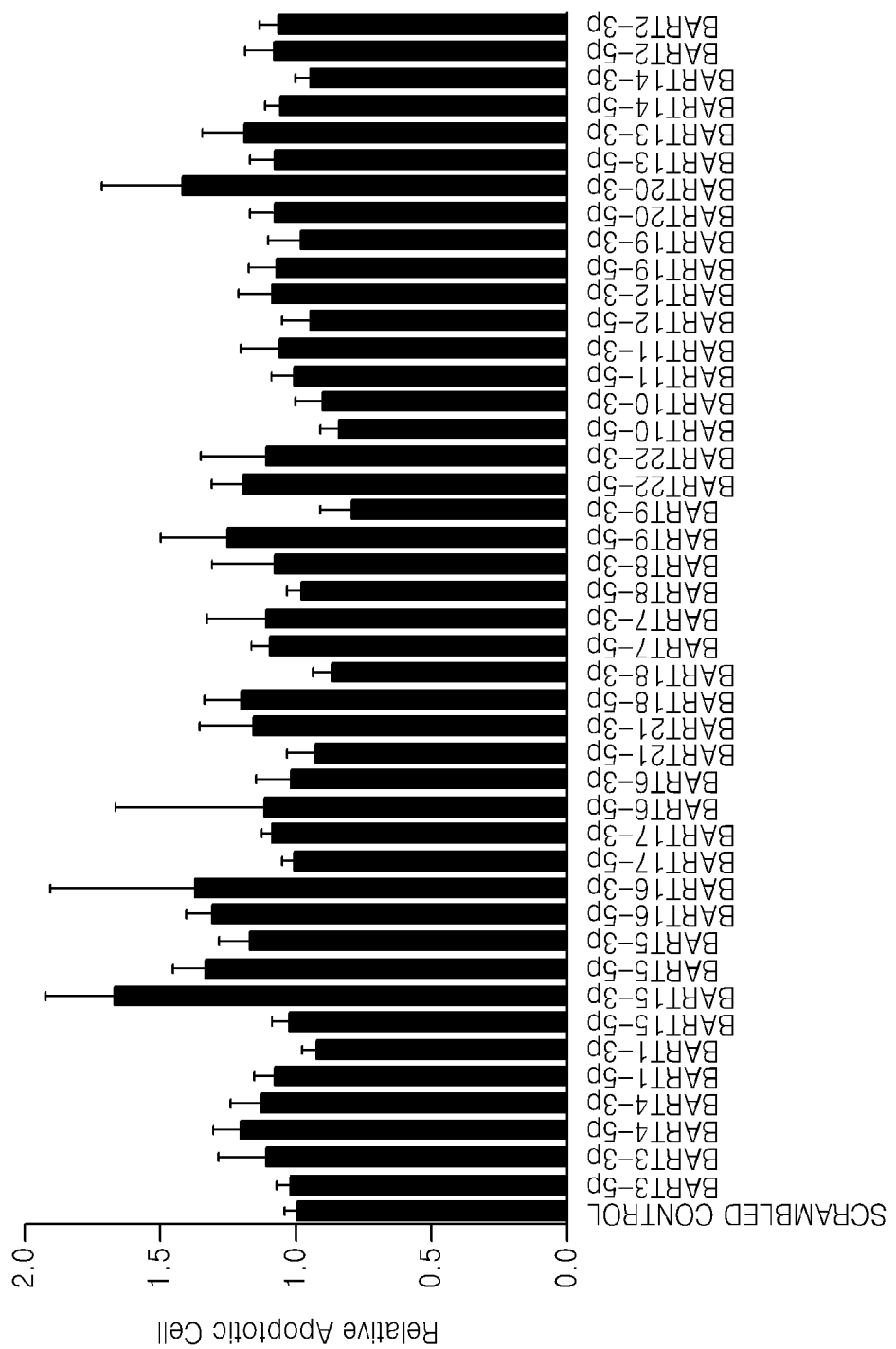
FIG. 8 shows the apoptosis effect on an AGS cell strain investigated by Annexin V staining when individual BART miRNA mimics were treated with 5-FU simultaneously. n=9, *:P<0.05, †: P<0.01.

Staining with Annexin V, which is a fluorescent pigment which may stain an external surface of a cell in which apoptosis is induced, was significantly higher in the cells to which synthesized miR-BART4-5p, 4-3p, 1-5p, 15-3p, 5-5p, 16-5p, 16-3p, 17-3p, 21-3p, 18-5p, 7-5p, 9-5p, 22-5p, 20-3p, 13-5p, 13-3p, and 2-3p mimics were transfected than that of the cell to which a scrambled control was transfected (Table 5 and FIG. 8).

TABLE 5

|  | Relative Apoptotic cell | Standard Deviation | p value |
|---|---|---|---|
| Scrambled control | 1 | ±0.045449 |  |
| BART3-5p | 1.015518 | ±0.057258 | 0.533833207 |
| BART3-3p | 1.111229 | ±0.179385 | 0.104858241 |
| BART4-5p | 1.203786 | ±0.098988 | 0.0001573 |
| BART4-3p | 1.132958 | ±0.112067 | 0.007098806 |
| BART1-5p | 1.080029 | ±0.076102 | 0.017899831 |
| BART1-3p | 0.923128 | ±0.05671 | 0.006299649 |
| BART15-5p | 1.022471 | ±0.067605 | 0.42180601 |
| BART15-3p | 1.664526 | ±0.262502 | 7.03897E-05 |
| BART5-5p | 1.325288 | ±0.131761 | 3.70881E-05 |
| BART5-3p | 1.170317 | ±0.118036 | 0.002362445 |
| BART16-5p | 1.311740 | ±0.095923 | 2.57932E-06 |
| BART16-3p | 1.369744 | ±0.531194 | 0.071050536 |
| BART17-5p | 1.003707 | ±0.045914 | 0.865469677 |
| BART17-3p | 1.087938 | ±0.038403 | 0.000417 |
| BART6-5p | 1.116871 | ±0.553642 | 0.545540951 |
| BART6-3p | 1.018077 | ±0.126517 | 0.695135495 |
| BART21-5p | 0.920701 | ±0.110456 | 0.071812901 |
| BART21-3p | 1.155482 | ±0.199968 | 0.048993185 |
| BART18-5p | 1.201565 | ±0.139068 | 0.002034155 |
| BART18-3p | 0.870541 | ±0.072638 | 0.000562715 |
| BART7-5p | 1.096568 | ±0.072284 | 0.00480732 |
| BART7-3p | 1.106590 | ±0.223946 | 0.195211986 |
| BART8-5p | 0.975743 | ±0.05407 | 0.318217 |
| BART8-3p | 1.072157 | ±0.238263 | 0.395391 |
| BART9-5p | 1.249817 | ±0.252558 | 0.017017 |
| BART9-3p | 0.794846 | ±0.11368 | 0.000516 |
| BART22-5p | 1.196878 | ±0.120093 | 0.00098 |
| BART22-3p | 1.105684 | ±0.247556 | 0.239469 |
| BART10-5p | 0.837272 | ±0.066876 | 3.05E-05 |
| BART10-3p | 0.897144 | ±0.108305 | 0.023527 |
| BART11-5p | 1.005647 | ±0.085212 | 0.863686 |
| BART11-3p | 1.058308 | ±0.148333 | 0.288678 |
| BART12-5p | 0.945826 | ±0.106574 | 0.188281 |
| BART12-3p | 1.084376 | ±0.129566 | 0.095047 |
| BART19-5p | 1.071132 | ±0.109755 | 0.099917 |
| BART19-3p | 0.974170 | ±0.127526 | 0.5797 |
| BART20-5p | 1.074948 | ±0.102514 | 0.07019 |
| BART20-3p | 1.415718 | ±0.298863 | 0.003319 |
| BART13-5p | 1.077471 | ±0.092429 | 0.043486 |
| BART13-3p | 1.186893 | ±0.15828 | 0.007815 |
| BART14-5p | 1.053543 | ±0.062082 | 0.054294 |
| BART14-3p | 0.942639 | ±0.062966 | 0.042576 |
| BART2-5p | 1.081581 | ±0.108739 | 0.062056 |
| BART2-3p | 1.061974 | ±0.070423 | 0.043585 |

Although an antisense sequence of a synthesized double stranded RNA is known to be almost degraded, a remaining antisense sequence of miR-BART4-5p, miR-BART15-3p, miR-BART5-5p, miR-BART16-5p, miR-BART17-3p, miR-BART9-5p, and miR-BART20-3p which is not degraded may function as siRNA. Thus, a siDirect software program analyzing an off-target effect of a double stranded RNA was used to investigate the possibility of off-target effect. The result showed that the antisense sequences included at least two mismatches, and thus antisense sequences are deemed to have no possibility to act as a siRNA.

EXAMPLE 10

Selection of Expected Target Genes of miR-BART15-3p

Figure 10:
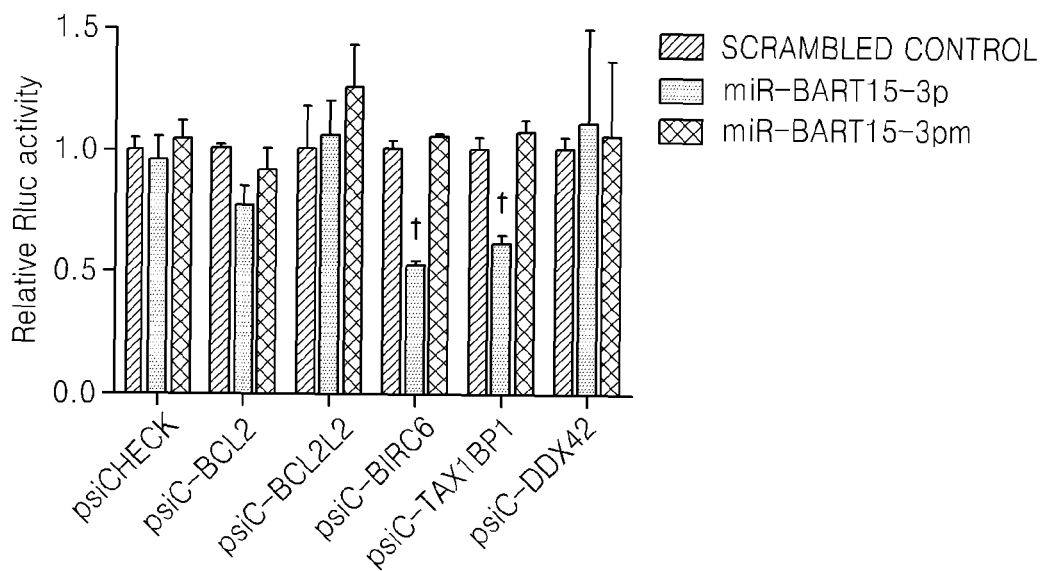

A software program of scanning expected target genes of an miRNA, such as Targetscan (http://www.targetscan.org/), Reptar (http://bioinformatics.ekmd.huji.ac.il/reptar/), or DIANA-microT (http://diana.cslab.ece.ntua.gr/microT/) was used to make a list of expected target genes, investigate functions of individual expected target genes, and genes related to apoptosis were separated. Then, a degree of hybridization between target sites of the expected target genes and miR-BART15-3p was investigated with a RNA hybrid software program (http://bibiserv.techfak.uni-bielefeld.de/rnahybrid/). The result of the RNA hybridization of the finally selected genes is shown in Table 6.

was performed to normalize the results with reference to firefly luciferase and observe a variation of the renilla luciferase gene expression. Among the five candidate genes of the experiment, only the psiCHECK vector to which 3'UTR of BIRC6 and TAX1BP1 was introduced showed a decrease of the renilla value by miR-BART15-3p. The renilla value was not decreased by miR-BART15-3 μm which was formed by mutating a seed part of miR-BART15-3p (FIG. 10). This result indicates that miR-BART15-3p targeted 3'UTR of BIRC6 and TAX1BP1 to decrease expression of renilla luciferase gene.

Figure 11:
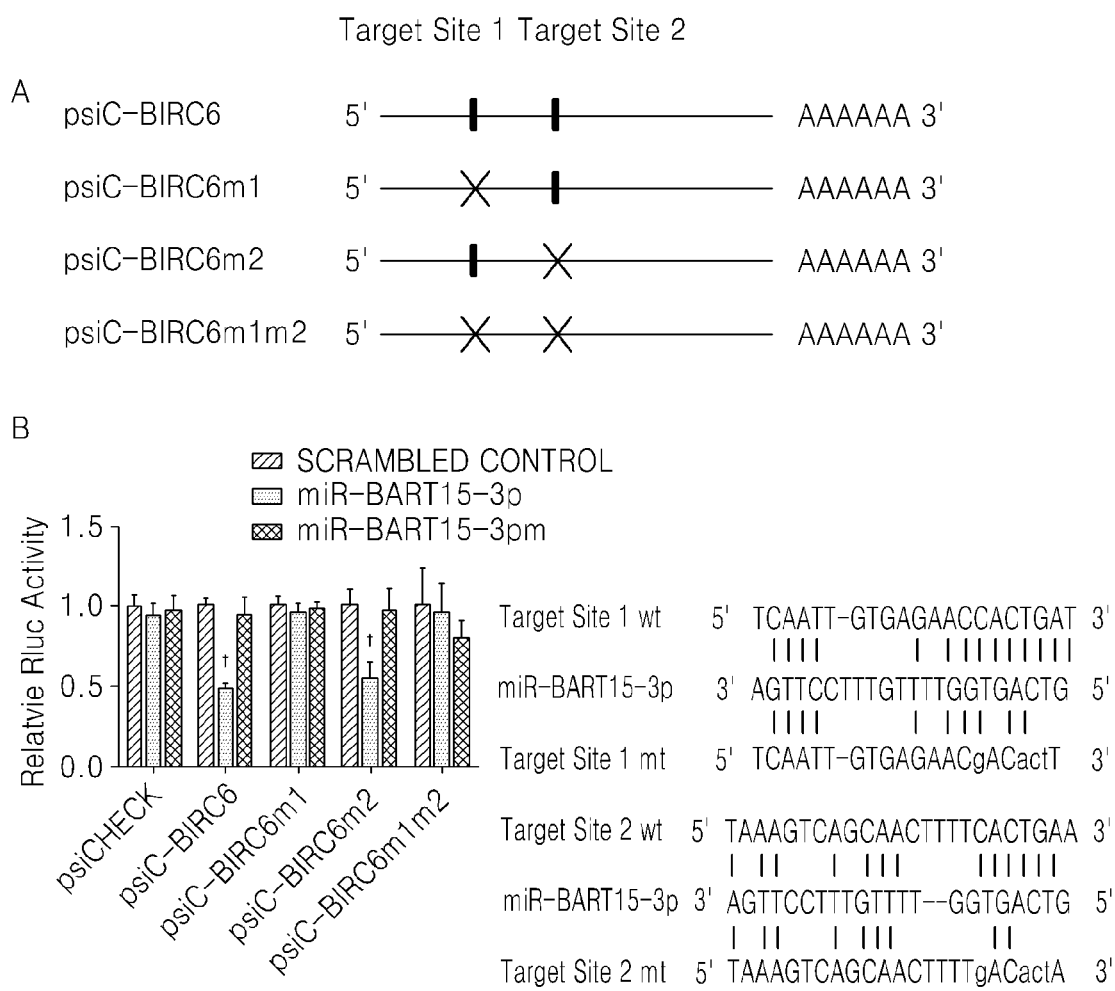
FIG. 11 shows the result of verifying whether miR-BART15-3p direct targets BIRC6 3'UTR. A shows the expected binding sites of miR-BART15-3p included in psiC-BIRC6, BIRC6m1, BIRC6m2, and BIRC6m1m2. B shows the result of a luciferase reporter assay performed after delivering each vector and miR-BART15-3p together into an HEK293T cell.

BIRC6 3'UTR included two target sites which might be hybridized with miR-BART15-3p. To verify whether these two sites are directly targeted by miR-BART15-3p, a point mutation was performed at a psiC-BIRC6 site which was seed-matched with miR-BART15-3p to prepare psiC-BIRC6m1 and psiC-BIRC6m2. Both of the sites were mutated to prepare psiC-BIRC6m1m2 (FIG. 11A).

HEK293T was divided into a 96-well plate such that 5×10³ cells were allocated to each well, and miR-BART15-3p and a

TABLE 6

```
Expected
Target
Gene      Function            Schematic Diagram of Hybridization
                              between Target Site and miRNA BCL2      anti-               target 5' A CU    UGU   CU           G 3'
          apoptotic                      C   GGA    CA  GGCCACUGA
          gene                           G   CCU    GU  UUGGUGACU
                              miRNA  3' A UU    UU    U            G 5'

BCL2L2    BCL2 type            target 5' A CU    UGU   CU           G 3'
          anti-apoptotic                 C   GGA    CA  GGCCACUGA
          gene                           G   CCU    GU  UUGGUGACU
                              miRNA  3' A UU    UU    U            G 5'

BIRC6     protecting cell     target 5' U    UU  UG              U 3'
          under apoptosis               UCAA   G  AGAACCACUGAU
                                        AGUU   U  UUUUGGUGACUG
                              miRNA  3'      CCU UG                 5' target 5' A    UC      CUUU        A 3'
                                        AAG  AGCAA   UCACUGA
                                        UUC  UUGUU   GGUGACU
                              miRNA  3' AG   CU      UU          G 5'

TAX1BP1   inhibiting           target 5'   A                       G 3'
          TNF-induced                      AAAU AGACCACUGA
          apoptosis                        UUUG UUUGGUGACU
                              miRNA  3' AGUUCC    U                G 5'

DDX42     increasing cell      target 5' U    UUGGCUUCU    UUCAAU    G 3'
          survival by                    AGGAG          GCAAA     CCAUUGA
          interacting with                UCCUU          UGUUU     GGUGACU
          TP53BP2             miRNA  3' AGU              U              G 5'
```

EXAMPLE 11

Test of Expected Target Genes of miR-BART15-3p

Figure 9:
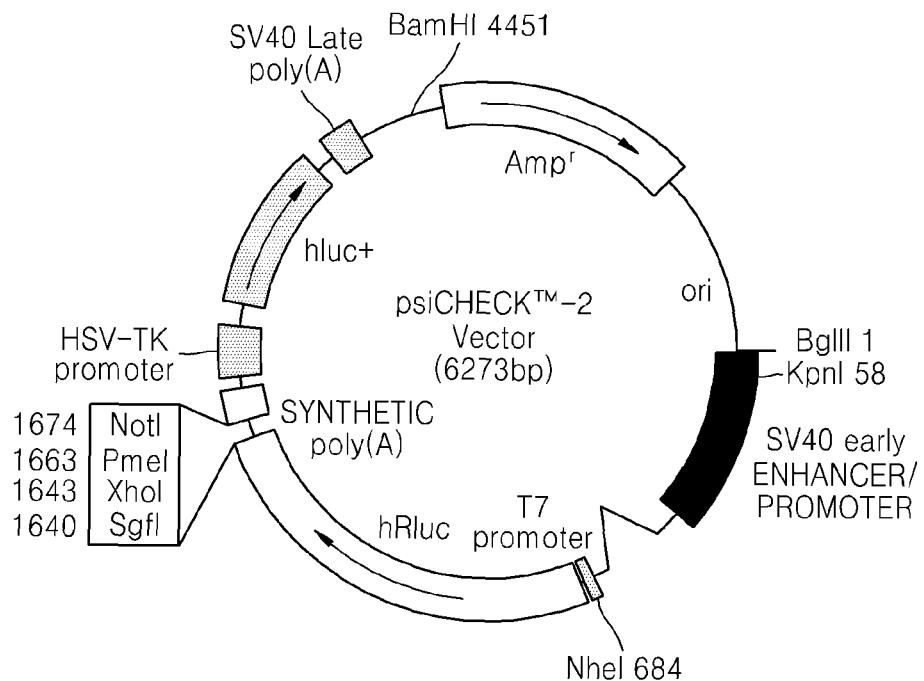
FIGS. 9 and 10 show the results of verifying whether a gene which might be targeted by miR-BART15-3p was actually targeted. The top shows a schematic diagram of psiCHECK which is specially designed for an miRNA targeting test. The bottom shows the result of testing a gene which might be targeted by miR-BART15-3p performed by a luciferase reporter assay. n=3; †: P<0.01.

For an miRNA target test, to psiCHECK, which is a luciferase vector (FIG. 9) specially designed for an miRNA target test including a firefly gene and a renilla gene in the same vector, a 3'UTR of the five genes shown in Table 5, which might be targeted by miR-BART15-3p, was individually cloned to prepare a vector for a target test for each of the genes.

HEK293T was divided into a 96-well plate such that 5×10³ cells were allocated to each well, and miR-BART15-3p and a vector for a target test were transfected by using lipofectamine2000. Forty eight hours after the transfection, a dual luciferase reporter assay (Virology. 412(2), 392-400 (2011))

vector for a target test were transfected by using lipofectamine-2000. Forty eight hours after the transfection, a dual luciferase reporter assay (Virology. 412(2), 392-400 (2011)) was performed to normalize the results with reference to firefly luciferase and observe a variation of the renilla luciferase gene expression. The renilla value was not decreased in psiC-BIRC6m1 and psiC-BIRC6m1m2 by, while the renilla value was decreased in psiC-BIRC6m2 as in the case of psiC-BIRC6. The result indicates that miR-BART15-3p directly targets only a mutation site in psiC-BIRC6m1 among the two expected binding sites in BIRC6 (FIG. 11B).

EXAMPLE 12

Effect of miR-BART15-3p on Expression of Target Gene

Figure 12:
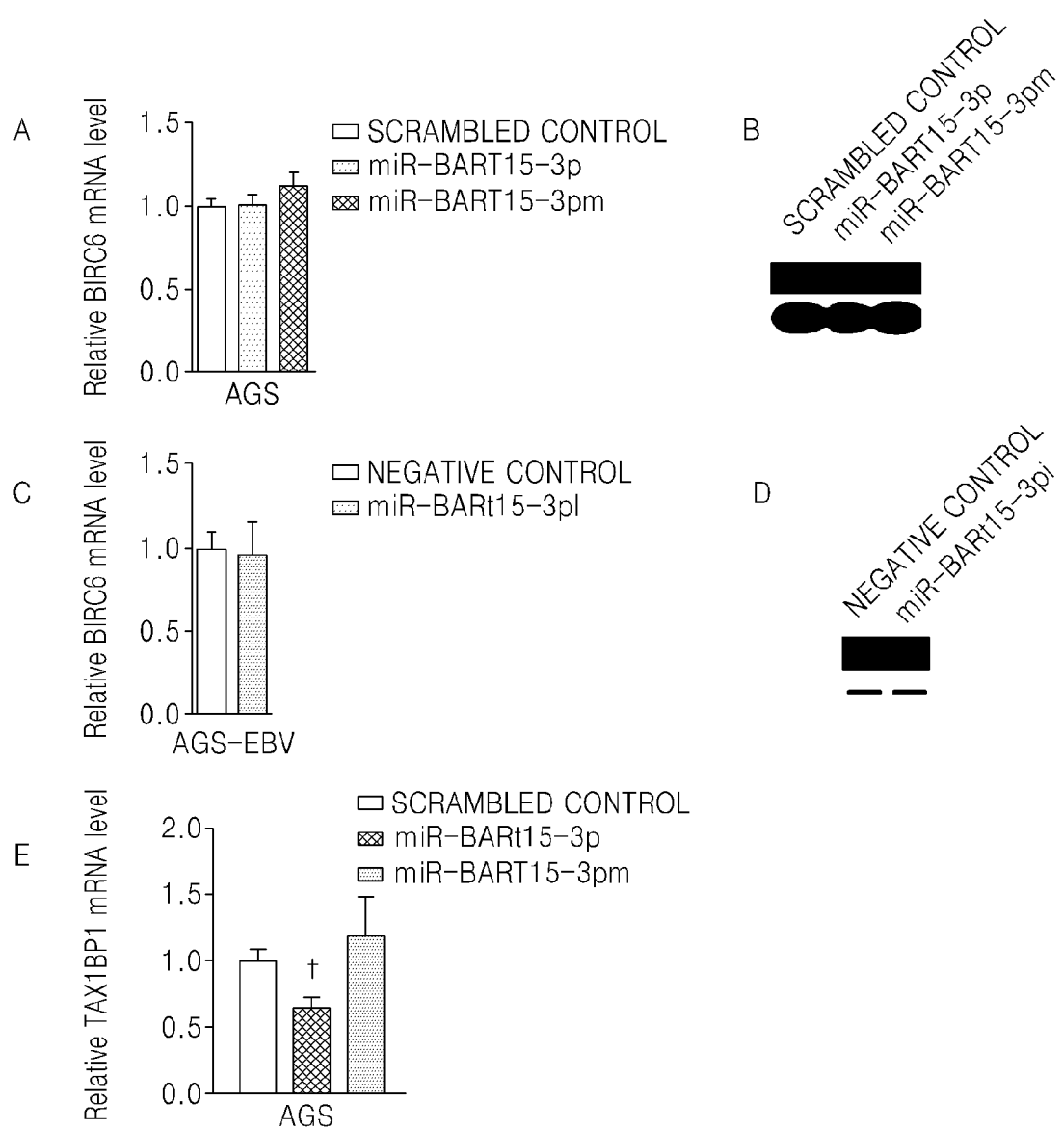
FIG. 12 shows the effect of miR-BART15-3p on mRNA and protein levels of genes which were identified as a target. A. BIRC6 mRNA level verified by QRT-PCR in an AGS to which miR-BART15-3p was delivered. B. BIRC6 protein level verified by Western blotting in an AGS to which miR-BART15-3p was delivered. C. BIRC6 mRNA level verified by QRT-PCR in an AGS-EBV to which an miR-BART15-3p inhibitor was delivered. D. BIRC6 protein level verified by Western blotting in an AGS-EBV to which an miR-BART15-3p inhibitor was delivered. E. TAX1BP1 mRNA level verified by QRT-PCR in an AGS to which miR-BART15-3p was delivered.

It was investigated whether the mRNA level and the protein level of BIRC6, which was considered as a direct target of miR-BART15-3p, were changed by miR-BART15-3p.

miR-BART15-3p was transfected to AGS by using lipofectamine-2000. Forty eight hours after the transfection, the cells were harvested and a QRT-PCR and a Western blotting were performed (FIGS. 12A and 12B). The BIRC6 mRNA level was not changed in the AGS to which miR-BART15-3p was transfected, while the protein level was decreased.

An miR-BART15-3p inhibitor was transfected to AGS-EBV by using lipofectamine-2000. Forty eight hours after the transfection, the cells were harvested and a QRT-PCR and a Western blotting were performed (FIGS. 12C and 12D). The BIRC6 mRNA level was not changed in the AGS-EBV to which an miR-BART15-3p inhibitor was transfected, while the protein level was increased.

Different from BIRC6, the mRNA level of TAX1BP1 was decreased in the AGS to which miR-BART15-3p was transfected (FIG. 12E).

---

The invention claimed is:

1. A method for promoting apoptosis or inhibiting cell growth, the method comprising administering to a subject in need thereof an effective amount of miR-BART15-3p.

2. The method for promoting apoptosis or inhibiting cell growth of claim 1, wherein the mimics is an miR-BART15-3p mimic to which an RNA having a sequence of SEQ NO:15 and an RNA having a sequence of SEQ NO:16 are hybridized.

3. The method of claim 1, wherein the miR-BART15-3P is included in a recombinant plasmid or viral vector expressing miR-BART15-3P included in a nonviral vector.

* * * * *